United States Patent
Zhan et al.

(10) Patent No.: US 11,610,679 B1
(45) Date of Patent: Mar. 21, 2023

(54) PREDICTION AND PREVENTION OF MEDICAL EVENTS USING MACHINE-LEARNING ALGORITHMS

(71) Applicant: Health at Scale Corporation, San Jose, CA (US)

(72) Inventors: Tiange Zhan, Mountain View, CA (US); Dahee Lee, San Jose, CA (US); John Guttag, Lexington, MA (US); Zeeshan Syed, Cupertino, CA (US)

(73) Assignee: Health at Scale Corporation, San Jose, CA (US)

( * ) Notice: Subject to any disclaimer, the term of this patent is extended or adjusted under 35 U.S.C. 154(b) by 113 days.

(21) Appl. No.: 16/853,621

(22) Filed: Apr. 20, 2020

(51) Int. Cl.
| | | |
|---|---|---|
| *G16H 50/20* | (2018.01) | |
| *G16H 50/30* | (2018.01) | |
| *G06N 7/01* | (2023.01) | |
| *G06N 20/20* | (2019.01) | |

(52) U.S. Cl.
CPC .............. *G16H 50/20* (2018.01); *G06N 7/01* (2023.01); *G06N 20/20* (2019.01); *G16H 50/30* (2018.01)

(58) Field of Classification Search
CPC ......... G16H 10/00–80/00; G06N 3/00–99/007
See application file for complete search history.

(56) References Cited

U.S. PATENT DOCUMENTS

| | | |
|---|---|---|
| 7,191,150 B1 | 3/2007 | Shao |
| 7,853,456 B2 | 12/2010 | Soto et al. |
| 8,417,541 B1 | 4/2013 | Kramer |
| 8,548,937 B2 | 10/2013 | Saigal et al. |
| 10,943,676 B2 * | 3/2021 | Farooq .................. G16H 40/20 |
| 11,114,204 B1 * | 9/2021 | Guttag .................. G16H 50/70 |

(Continued)

FOREIGN PATENT DOCUMENTS

| | | | |
|---|---|---|---|
| CA | 2715825 A1 | 8/2009 | |
| EP | 3382584 A1 * | 10/2018 | ............ G16H 50/20 |

(Continued)

OTHER PUBLICATIONS

Baechle et al., "Latent topic ensemble learning for hospital readmission cost optimization," European Journal of Operational Research 281 (2020) 517-531. (Year: 2019).*

(Continued)

*Primary Examiner* — Jonathon A. Szumny
(74) *Attorney, Agent, or Firm* — Morrison & Foerster LLP

(57) ABSTRACT

The present disclosure relates to providing personalized prediction and prevention of various types of medical events (e.g., emergency department visits, hospital admissions, complications) using machine-learning algorithms. An exemplary method comprises: obtaining a plurality of feature values of the patient; providing the plurality of feature values to a set of one or more trained machine-learning models to obtain: a first probabilistic value indicating a likelihood of a future medical event, a second probabilistic value indicating a likelihood of a reason for the future medical event, a third probabilistic value indicating a likelihood that the future medical event can be prevented, displaying, on the display, a risk value of the future medical event based on the first probabilistic value, a reason of the future medical event based on the second probabilistic value, an interceptability value of the future medical event based on the third probabilistic value.

15 Claims, 13 Drawing Sheets

(56) References Cited

U.S. PATENT DOCUMENTS

| | | |
|---|---|---|
| 2003/0135128 A1 | 7/2003 | Suffin |
| 2004/0107088 A1 | 6/2004 | Budzinski |
| 2006/0173663 A1 | 8/2006 | Langheier |
| 2006/0206359 A1 | 9/2006 | Stang |
| 2007/0088577 A1 | 4/2007 | Carter et al. |
| 2007/0269804 A1 | 11/2007 | Liew |
| 2009/0093689 A1 | 4/2009 | Schuppert et al. |
| 2009/0259550 A1 | 10/2009 | Mihelich |
| 2010/0184093 A1* | 7/2010 | Donovan .............. G16H 50/50 435/287.1 |
| 2011/0082712 A1 | 4/2011 | Eberhardt, III |
| 2011/0295621 A1* | 12/2011 | Farooq .................. G16H 50/20 705/3 |
| 2012/0041330 A1* | 2/2012 | Prichep ................. A61B 5/291 600/544 |
| 2012/0066217 A1 | 3/2012 | Eder |
| 2012/0095943 A1 | 4/2012 | Yankov |
| 2012/0109683 A1 | 5/2012 | Ebadollahi |
| 2012/0179002 A1 | 7/2012 | Brunetti et al. |
| 2013/0022953 A1 | 1/2013 | Van |
| 2013/0096948 A1 | 4/2013 | Parkinson |
| 2013/0185096 A1 | 7/2013 | Giusti |
| 2013/0197925 A1 | 8/2013 | Blue |
| 2013/0225439 A1* | 8/2013 | Princen ............. G01N 33/6893 506/9 |
| 2014/0058755 A1 | 2/2014 | Macoviak |
| 2014/0108034 A1 | 4/2014 | Akbay |
| 2014/0200824 A1 | 7/2014 | Pancoska |
| 2014/0371610 A1* | 12/2014 | Liu ........................ A61B 5/316 600/509 |
| 2015/0006456 A1* | 1/2015 | Sudharsan ............. G06N 5/048 706/46 |
| 2015/0046181 A1 | 2/2015 | Adjaoute |
| 2015/0073943 A1 | 3/2015 | Norris et al. |
| 2015/0100336 A1 | 4/2015 | Ford et al. |
| 2015/0100349 A1* | 4/2015 | Lacy ..................... G16H 10/60 705/3 |
| 2015/0161331 A1 | 6/2015 | Oleynik |
| 2015/0164453 A1* | 6/2015 | Choi ..................... G06T 7/0012 600/407 |
| 2015/0248534 A1* | 9/2015 | Krzywicki .......... G06F 3/04847 715/771 |
| 2015/0278470 A1 | 10/2015 | Bakker |
| 2015/0289795 A1 | 10/2015 | Batlle |
| 2015/0294075 A1 | 10/2015 | Rinaldo |
| 2015/0317449 A1 | 11/2015 | Eder |
| 2015/0367145 A1 | 12/2015 | Sjölund et al. |
| 2016/0012202 A1 | 1/2016 | Hu et al. |
| 2016/0135706 A1* | 5/2016 | Sullivan ................. A61N 1/046 600/509 |
| 2016/0147959 A1* | 5/2016 | Mariottini .............. G16H 50/20 706/46 |
| 2016/0196398 A1* | 7/2016 | Vivero ................... G16H 15/00 705/2 |
| 2016/0203217 A1 | 7/2016 | Anisingaraju et al. |
| 2016/0259883 A1 | 9/2016 | Grinchuk et al. |
| 2016/0378943 A1* | 12/2016 | Vallée .................... G16H 40/63 705/2 |
| 2017/0073761 A1 | 3/2017 | Harkin et al. |
| 2017/0083682 A1 | 3/2017 | Mcnutt |
| 2017/0101093 A1* | 4/2017 | Barfield, Jr. ........... G08G 1/164 |
| 2017/0124269 A1 | 5/2017 | Mcnair |
| 2017/0185723 A1 | 6/2017 | Mccallum et al. |
| 2017/0277856 A1 | 9/2017 | De La Torre et al. |
| 2017/0308671 A1* | 10/2017 | Bahrami ................ G16H 10/60 |
| 2018/0121619 A1 | 5/2018 | Perlroth et al. |
| 2018/0214105 A1* | 8/2018 | Anavi .................... G06V 10/82 |
| 2019/0043606 A1 | 2/2019 | Roots et al. |
| 2019/0172587 A1* | 6/2019 | Park ....................... G16H 50/50 |
| 2019/0333613 A1 | 10/2019 | Zaidi et al. |
| 2019/0371450 A1 | 12/2019 | Lou et al. |
| 2020/0074313 A1* | 3/2020 | Sharifi Sedeh ........ G06N 20/00 |
| 2021/0035693 A1* | 2/2021 | Mohammad ........... G16H 50/30 |
| 2021/0065909 A1* | 3/2021 | Donaldson ............. G16H 50/30 |
| 2021/0118559 A1* | 4/2021 | Lefkofsky .............. G16H 30/20 |
| 2021/0221404 A1* | 7/2021 | Reiner ................... G05D 1/0055 |
| 2021/0249138 A1* | 8/2021 | Hayashitani ........... G06N 20/00 |

FOREIGN PATENT DOCUMENTS

| | | | | |
|---|---|---|---|---|
| JP | 2017174406 A | | 9/2017 | |
| WO | 2015157576 A1 | | 10/2015 | |
| WO | WO-2016120955 A1 | * | 8/2016 | ............. G06N 20/00 |
| WO | WO-2019212005 A1 | * | 11/2019 | ........... A61B 5/1117 |
| WO | WO-2020081609 A1 | * | 4/2020 | ........... A61B 5/0075 |

OTHER PUBLICATIONS

Rahimian et al., "Predicting the risk of emergency admission with machine learning: Development and validation using linked electronic health records," PLOS Medicine, Nov. 20, 2018, pp. 1-18 (Year: 2018).*

Sebastian Ruder, "An Overview of Multi-Task Learning in Deep Neural Networks," https://ruder.io/multi-task/ (Year: 2017).*

Li et al., "Lung Nodule Malignancy Prediction Using Multi-task Convolutional Neural Network," Proc. of SPIE vol. 10134 1013424-1 (Year: 2017).*

Caruana, Rich. (1997). "Multitask Learning," Kluwer Academic Publishers, Manufactured in the Netherlands, Machine Learning, 35 pages.

Caruana, Rich. (May 1996). "Algorithms and Applications for Multitask Learning," School of Computer Science, Carnegie Mellon University, Pittsburgh, PA, 9 pages.

Non-Final Office Action dated Aug. 17, 2021, for U.S. Appl. No. 14/622,112, filed Feb. 13, 2015, 11 pages.

Non-Final Office Action dated Aug. 27, 2021, for U.S. Appl. No. 14/809,528, filed Jul. 27, 2015, 14 pages.

Final Office Action dated Nov. 16, 2020, for U.S. Appl. No. 14/736,470, filed Jun. 11, 2015, eleven pages.

Bretthauer, K. M., & Cote, M. J. (1998). A model for planning resource requirements in health care organizations. Decision Sciences, 29(1), 243-270. Retrieved from https://search.proquest.com/docview/198106120?accountid=14753 (Year: 1998).

Final Office Action dated Dec. 26, 2018, for U.S. Appl. No. 14/809,528, filed Jul. 27, 2015, 30 pages.

Final Office Action dated Jan. 7, 2019, for U.S. Appl. No. 14/736,470, filed Jun. 11, 2015, fifteen pages.

Final Office Action dated Jul. 23, 2018, for U.S. Appl. No. 14/622,112, filed Feb. 13, 2015, eleven pages.

Final Office Action dated May 3, 2018, for U.S. Appl. No. 14/678,349, filed Apr. 3, 2015, twenty one pages.

Non-Final Office Action dated Dec. 18, 2019, for U.S. Appl. No. 14/678,349, filed Apr. 3, 2015, eleven pages.

Non-Final Office Action dated Feb. 26, 2018, for U.S. Appl. No. 14/736,470, filed Jun. 11, 2015, sixteen pages.

Non-Final Office Action dated Jan. 10, 2019, for U.S. Appl. No. 14/678,349, filed Apr. 3, 2015, twenty two pages.

Non-Final Office Action dated Jan. 29, 2020, for U.S. Appl. No. 14/809,528, filed Jul. 27, 2015, 20 pages.

Non-Final Office Action dated Mar. 14, 2019, for U.S. Appl. No. 14/622,112, filed Feb. 13, 2015, ten pages.

Non-Final Office Action dated Mar. 27, 2020, for U.S. Appl. No. 14/622,112, filed Feb. 13, 2015, nine pages.

Non-Final Office Action dated Mar. 9, 2020, for U.S. Appl. No. 14/736,470, filed Jun. 11, 2015, nine pages.

Non-Final Office Action dated May 1, 2018, for U.S. Appl. No. 14/809,528, filed Jul. 27, 2015, 25 pages.

Non-Final Office Action dated Sep. 22, 2017, for U.S. Appl. No. 14/678,349, filed Apr. 3, 2015, thirteen pages.

Non-Final Office Action dated Sep. 28, 2017, for U.S. Appl. No. 14/622,112, filed Feb. 13, 2015, fifteen pages.

Final Office Action dated Jul. 21, 2020, for U.S. Appl. No. 14/678,349, filed Apr. 3, 2015, twelve pages.

Final Office Action dated Jul. 21, 2020, for U.S. Appl. No. 14/809,528, filed Jul. 27, 2015, twenty pages.

(56) References Cited

OTHER PUBLICATIONS

Notice of Allowance dated Jul. 28, 2021, for U.S. Appl. No. 14/678,349, filed Apr. 3, 2015, eleven pages.
Final Office Action dated Dec. 21, 2020, for U.S. Appl. No. 14/622,112, filed Feb. 13, 2015, nine pages.
Non-Final Office Action dated Jan. 29, 2021, for U.S. Appl. No. 14/678,349, filed Apr. 3, 2015, eight pages.
Non-Final Office Action dated Mar. 18, 2022, for U.S. Appl. No. 14,736,470, filed Jun. 11, 2015, 14 pages.
Brakenhoff, T. B., et al. (2018). "Investigating Risk Adjustment Methods for Health Care Provider Profiling When Observations are Scarce or Events Rare". Health Services Insights, vol. 11, 1-10, doi: http://dx.doi.org/10.1177/1178632918785133 , (Year:2018).
Final Office Action dated Oct. 4, 2022, for U.S. Appl. No. 14/736,470, filed Jun. 11, 2015, thirteen pages.
Non-Final Office Action dated Jul. 27, 2022, for U.S. Appl. No. 16/875,835, filed May 15, 2020, 48 pages.
Notice of Allowance dated Sep. 6, 2022, for U.S. Appl. No. 14/622,112, filed Feb. 13, 2015, nine pages.
Tan, Kar Way. "Dynamic Queue Management for Hospital Emergency Room Services." Order No. 10169843 Singapore Management University (Singapore), 2013. Ann Arbor: ProQuest. Web., Aug. 25, 2022. (Year: 2013).
Notice of Allowance dated Nov. 7, 2022, for U.S. Appl. No. 14/622,112, filed Feb. 13, 2015, nine pages.
Non-Final Office Action dated Dec. 14, 2022, for U.S. Appl. No. 14/809,528, filed Jul. 27, 2015, fifteen pages.

* cited by examiner

Filters 122

[State ▽]

[Plain Type ▽]

Emergency Department Vsits 120

All | Assigned to me | Unassigned 124

Review Status
○ Reviewed
◉ Unreviewed

[Clinical Risk Factor ▽]

Interceptability
☐ Low
☐ Medium
☐ High

| Name | Member ID | Risk | Interceptability | Assignment |
|---|---|---|---|---|
| Andrea Adams | 1234567890 | 5 | 3-High | Jane Doe |
| Robert Anderson | 1234567891 | 1 | 2-Medium | Unassigned |
| James Baker | 1234567892 | 3 | 3-High | Kristina Miller |
| Brad Brandt | 1234567893 | 5 | 3-Low | Unassigned |

« Previous [1] 2 3 4 5 ... 10 Next »

Brad Brandt
Member ID: 181964462 | Residence: Castroburgh, Arizona

| | |
|---|---|
| Risk | 5 |
| Interceptability | 3 |
| Assignment Status | Unassigned |
| Clinical Risk Factor | Cough |
| Prior ED Visits | 0 |
| Plan Type | Medicaid |
| Review Status | Reviewed |

Assignment Status ☐ Assign to Me

CANCEL    UPDATE

FIG. 1C

Feature Set 220

Patient i - Jan-Dec 2015

| Age | Past ED Visits | Procedures | ... | Diagnoses |

Outcome Set 222

Patient i - Jan-June 2016

| Has ED Visits | Reasons for ED Visits | ... |

502
OBTAINING A PLURALITY OF FEATURE VALUES OF THE PATIENT

504
PROVIDING THE PLURALITY OF FEATURE VALUES TO A SET OF ONE OR MORE TRAINED MACHINE-LEARNING MODELS TO OBTAIN:

A FIRST PROBABILISTIC VALUE INDICATING A LIKELIHOOD OF A FUTURE MEDICAL EVENT,

A SECOND PROBABILISTIC VALUE INDICATING A LIKELIHOOD OF A REASON FOR THE FUTURE MEDICAL EVENT,

A THIRD PROBABILISTIC VALUE INDICATING A LIKELIHOOD THAT THE FUTURE MEDICAL EVENT CAN BE PREVENTED,

506
DISPLAYING, ON THE DISPLAY,

A RISK VALUE OF THE FUTURE MEDICAL EVENT BASED ON THE FIRST PROBABILISTIC VALUE,

A REASON OF THE FUTURE MEDICAL EVENT BASED ON THE SECOND PROBABILISTIC VALUE,

AN INTERCEPTABILITY VALUE OF THE FUTURE MEDICAL EVENT BASED ON THE THIRD PROBABILISTIC VALUE

FIG. 5

PREDICTION AND PREVENTION OF MEDICAL EVENTS USING MACHINE-LEARNING ALGORITHMS

FIELD OF THE INVENTION

The present disclosure relates generally to predictive diagnostics, and more specifically to providing personalized prediction and prevention of various types of medical events (e.g., emergency department visits, hospital admissions, complications) using machine-learning algorithms.

BACKGROUND

The rate of emergency department ("ED") visits has significantly increased in recent years. Combined with the rising cost of an average ED visit, this increase has led to total ED spending growing 36% between 2013 and 2017. The high cost places a burden on patients, providers, and payers and imposes a significant drain on healthcare resources. Further, a high volume of ED visits greatly diminishes the quality of ED care, leading to ED crowding, long wait times, and added stress on staff detracting from care delivery to patients in need of true emergency care. It also puts patients at risk of adverse outcomes such as infections, since acutely ill and injured patients in the ED are at risk of both spreading and contracting infections among themselves and healthcare personnel.

However, it is estimated that the majority of ED visits (as well as other types of medical events such as hospital admissions and complications) can be prevented through a combination of proactive and preemptive care, such as improvements in primary care, mental health care, substance abuse prevention, transportation and housing for patients, and more cost-effective outpatient alternatives. For example, in a recent study by the Centers for Disease Control and Prevention (CDC), 79% of ED visitors cited lack of timely access to other providers as a reason for their last ED visit, a situation that could potentially be remedied through earlier prediction and prevention of the need for medical care.

Many other medical events are similar to ED visits in terms of imposing immense burden on the healthcare system while being preventable during the early stages. This includes, for example, inpatient admissions, hospital readmissions, progression of chronic disease, complications of chronic disease, exacerbation of health conditions and state, high cost (e.g., resulting from increased utilization), and transition from low cost to high cost.

BRIEF SUMMARY

An exemplary computer-implemented method for providing personalized predictions of medical events for a patient, comprises: at an electronic device with a display, obtaining a plurality of feature values of the patient; providing the plurality of feature values to a set of one or more trained machine-learning models to obtain: a first probabilistic value indicating a likelihood of a future medical event, a second probabilistic value indicating a likelihood of a reason for the future medical event, a third probabilistic value indicating a likelihood that the future medical event can be prevented, displaying, on the display, a risk value of the future medical event based on the first probabilistic value, a reason of the future medical event based on the second probabilistic value, an interceptability value of the future medical event based on the third probabilistic value.

In some embodiments, the set of one or more trained machine-learning models is trained with a set of training data comprising: for each patient of a plurality of patients: a feature set corresponding to respective patient and a first time period, and an outcome set corresponding to the respective patient and a second time period.

In some embodiments, the set of one or more trained machine-learning models comprises a single machine-learning model.

In some embodiments, the single machine-learning model is a neural network.

In some embodiments, the set of trained machine-learning models comprises multiple machine-learning models.

In some embodiments, the multiple machine-learning models are neural networks.

In some embodiments, the multiple machine-learning models are used in an ensemble learning architecture.

In some embodiments, the set of one or more trained machine-learning models comprises a first subset of machine-learning models and a second subset of machine-learning models, wherein the first subset of machine-learning models are trained using a subset of a plurality of features, and wherein outputs of the first subset of models are passed as input to the second subset of machine-learning models.

In some embodiments, the outputs of the second subset of machine-learning models are passed as input to a third subset of the set of one or more trained machine-learning models.

In some embodiments, the set of one or more trained machine-learning models comprises: a first single model for predicting a risk, a reason, and interceptability for a first medical event; and a second single model for predicting a risk, a reason, and interceptability for a second medical event.

In some embodiments, the set of one or more trained machine-learning models comprises: a first single model for predicting risks for a first medical event and a second medical event; a second single model for predicting reasons for the first medical event and the second medical event; and a third single model for predicting interceptabilities for the first medical event and the second medical event.

In some embodiments, the set of one or more machine-learning models comprises a plurality of machine-learning models with a shared structure.

In some embodiments, the set of one or more trained machine-learning models are trained by optimization for a multivariate error metric.

In some embodiments, the intercepability value is based on the reason of the future medical event.

In some embodiments, the first probabilistic value is indicative of a likelihood of the future medical event occurring within a predefined time period.

The method of claim 1, further comprising: automatically assigning the patient to an outreach effort based on the risk value of the future medical event or the reason of the future medical event.

In some embodiments, the displaying is responsive to a user selection of the medical event from a plurality of medial events.

In some embodiments, the medical event is a visit to an emergency department, a hospital admission, progression of chronic disease, complication of chronic disease, exacerbation of health conditions and state, or transition from low cost to high cost.

In some embodiments, the plurality of feature values comprises enrolment and demographic information of the patient, medical information of the patient, information of the patient's care providers, social determinants of health, epidemiological data, billing or claims history information or any combination thereof.

An exemplary electronic device comprises: a display; one or more processors; a memory; and one or more programs, wherein the one or more programs are stored in the memory and configured to be executed by the one or more processors, the one or more programs including instructions for: obtaining a plurality of feature values of the patient; providing the plurality of feature values to a set of one or more trained machine-learning models to obtain: a first probabilistic value indicating a likelihood of a future medical event, a second probabilistic value indicating a likelihood of a reason for the future medical event, a third probabilistic value indicating a likelihood that the future medical event can be prevented, displaying, on the display, a risk value of the future medical event based on the first probabilistic value, a reason of the future medical event based on the second probabilistic value, an interceptability value of the future medical event based on the third probabilistic value.

An exemplary non-transitory computer-readable storage medium stores one or more programs, the one or more programs comprising instructions, which when executed by one or more processors of an electronic device having a display, cause the electronic device to: obtain a plurality of feature values of the patient; provide the plurality of feature values to a set of one or more trained machine-learning models to obtain: a first probabilistic value indicating a likelihood of a future medical event, a second probabilistic value indicating a likelihood of a reason for the future medical event, a third probabilistic value indicating a likelihood that the future medical event can be prevented, display, on the display, a risk value of the future medical event based on the first probabilistic value, a reason of the future medical event based on the second probabilistic value, an interceptability value of the future medical event based on the third probabilistic value.

An exemplary computer-implemented method for providing personalized predictions of a medical event for a patient comprises: at an electronic device with a display, obtaining a plurality of feature values of the patient; providing the plurality of feature values to a first trained machine-learning model to obtain a first probabilistic value, wherein the first trained machine-learning model is configured to receive a plurality of features of a given patient and output a probabilistic value indicating a likelihood of a future medical event; providing the plurality of feature values to a second trained machine-learning model to obtain a set of probabilistic values, wherein the second trained machine-learning model is configured to receive the plurality of features of the given patient and output a probabilistic value indicating likelihoods of reasons for the future medical event; displaying, on the display, a risk value of the future medical event based on the first probabilistic value, a reason of the future medical event based on the second set of probabilistic values, and an interceptability value indicating the likelihood that the future medical event can be prevented.

In some embodiments, the method further comprises providing the plurality of feature values to a third trained machine-learning model to obtain a third probabilistic value, wherein the third trained machine-learning model is configured to receive the plurality of features of the given patient and output a probabilistic value indicating a likelihood that the future medical event can be prevented, wherein the intercepability value is based on the third probabilistic value.

In some embodiments, the method further comprises calculating the intercepability value based on the reason of the future medical event.

In some embodiments, the method further comprises automatically assigning the patient to an outreach effort based on the risk value of the future medical event or the reason of the future medical event.

In some embodiments, the displaying is responsive to a user selection of the medical event from a plurality of medial events.

In some embodiments, the medical event is a visit to an emergency department.

In some embodiments, the medical event is a hospital admission.

In some embodiments, the first trained model is a logistic regression model, a neural network, an ensemble model, or a combination thereof.

In some embodiments, the second trained model is a logistic regression model, a neural network, an ensemble model, or a combination thereof.

In some embodiments, the plurality of feature values comprises demographic information of the patient, medical information of the patient, and information of the patient's care providers.

In some embodiments, the first model and the second model are trained via multi-task learning.

In some embodiments, the first model is trained based on a feature set corresponding to a first time period and an outcome set corresponding to a second time period immediately following the first time period.

An exemplary computer-implemented method for providing personalized predictions of a medical event comprises: obtaining a set of training data comprising: a first feature set corresponding to a first patient and a first time period, a first outcome set corresponding to the first patient and a second time period after the first time period, a second feature set corresponding to a second patient and the first time period, a second outcome set corresponding to the second patient and the second time period, training a first machine-learning model based on the set of training data, wherein the first machine-learning model is configured to receive a plurality of features of a given patient and output a probabilistic value indicating a likelihood of a future medical event; training a second machine-learning model based on the set of training data, wherein the second machine-learning model is configured to receive the plurality of features of the given patient and output a probabilistic value indicating a likelihood of a reason for the future medical event, and wherein the first machine-learning model and the second machine-learning model are trained via multi-task learning.

In some embodiments, the first machine-learning model and the second machine-learning model are neural network models with a shared structure.

In some embodiments, the first machine-learning model comprises an ensemble model.

In some embodiments, each of the first feature set and the second feature set comprises demographic information of a respective patient, medical information of the respective patient, and information of the respective patient's care providers.

An exemplary electronic device comprises: one or more processors; a memory; a display; and one or more programs, wherein the one or more programs are stored in the memory and configured to be executed by the one or more processors, the one or more programs including instructions for: obtaining a plurality of feature values of the patient; providing the plurality of feature values to a first trained machine-learning model to obtain a first probabilistic value, wherein the first trained machine-learning model is configured to receive a plurality of features of a given patient and output a probabilistic value indicating a likelihood of a future medical event; providing the plurality of feature values to a second trained machine-learning model to obtain a second probabilistic value, wherein the second trained machine-learning model is configured to receive the plurality of features of the given patient and output a probabilistic value indicating a likelihood of a reason for the future medical event; displaying, on the display, a risk value of the future medical event based on the first probabilistic value, a reason of the future medical event based on the second probabilistic value, and an intercepability value indicating the likelihood that the future medical event can be prevented.

An exemplary non-transitory computer-readable storage medium stores one or more programs, the one or more programs comprising instructions, which when executed by one or more processors of an electronic device having a display, cause the electronic device to: obtain a plurality of feature values of the patient; provide the plurality of feature values to a first trained machine-learning model to obtain a first probabilistic value, wherein the first trained machine-learning model is configured to receive a plurality of features of a given patient and output a probabilistic value indicating a likelihood of a future medical event; provide the plurality of feature values to a second trained machine-learning model to obtain a second probabilistic value, wherein the second trained machine-learning model is configured to receive the plurality of features of the given patient and output a probabilistic value indicating a likelihood of a reason for the future medical event; and display, on the display, a risk value of the future medical event based on the first probabilistic value, a reason of the future medical event based on the second probabilistic value, and an intercepability value indicating the likelihood that the future medical event can be prevented.

An electronic device comprises: one or more processors; a memory; and one or more programs, wherein the one or more programs are stored in the memory and configured to be executed by the one or more processors, the one or more programs including instructions for: obtaining a set of training data comprising: a first feature set corresponding to a first patient and a first time period, a first outcome set corresponding to the first patient and a second time period after the first time period, a second feature set corresponding to a second patient and the first time period, a second outcome set corresponding to the second patient and the second time period, training a first machine-learning model based on the set of training data, wherein the first machine-learning model is configured to receive a plurality of features of a given patient and output a probabilistic value indicating a likelihood of a future medical event; training a second machine-learning model based on the set of training data, wherein the second machine-learning model is configured to receive the plurality of features of the given patient and output a probabilistic value indicating a likelihood of a reason for the future medical event, and wherein the first machine-learning model and the second machine-learning model are trained via multi-task learning.

An exemplary non-transitory computer-readable storage medium stores one or more programs, the one or more programs comprising instructions, which when executed by one or more processors of an electronic device, cause the electronic device to: obtain a set of training data comprising: a first feature set corresponding to a first patient and a first time period, a first outcome set corresponding to the first patient and a second time period after the first time period, a second feature set corresponding to a second patient and the first time period, a second outcome set corresponding to the second patient and the second time period, train a first machine-learning model based on the set of training data, wherein the first machine-learning model is configured to receive a plurality of features of a given patient and output a probabilistic value indicating a likelihood of a future medical event; train a second machine-learning model based on the set of training data, wherein the second machine-learning model is configured to receive the plurality of features of the given patient and output a probabilistic value indicating a likelihood of a reason for the future medical event, and wherein the first machine-learning model and the second machine-learning model are trained via multi-task learning.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 1B illustrates an exemplary user interface of a system for providing personalized prediction and prevention of various types of medical events, in accordance with some embodiments.

FIG. 1C illustrates an exemplary user interface of a system for providing personalized prediction and prevention of various types of medical events, in accordance with some embodiments.

FIG. 2B illustrates an exemplary feature-outcome pair, in accordance with some embodiments.

FIG. 5 depicts a block diagram of an exemplary process for providing personalized prediction and prevention of various types of medical events, in accordance with some embodiments.

DETAILED DESCRIPTION

Figure 1A:
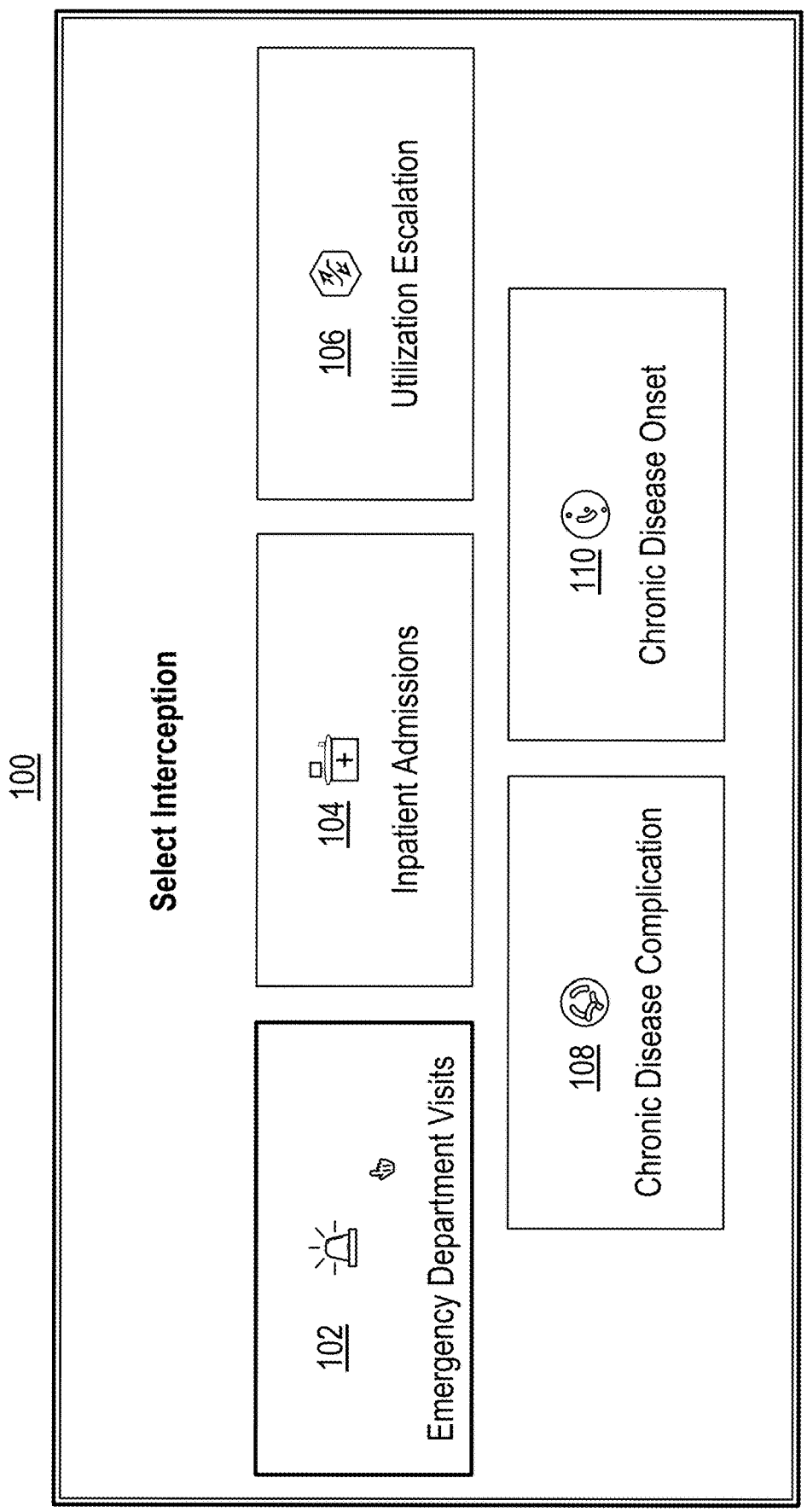
FIG. 1A illustrates an exemplary user interface of a system for providing personalized prediction and prevention of various types of medical events, in accordance with some embodiments.

The present disclosure is directed to systems, methods, devices, apparatus, and non-transitory storage media for providing personalized prediction and prevention of various types of medical events (e.g., ED visits, inpatient admissions, hospital readmissions, progression of chronic disease, complications of chronic disease, exacerbation of health conditions and state, high cost, and transition from low cost to high cost) using machine-learning algorithms. Embodiments of the present disclosure can go beyond examining past occurrence of a particular type of medical event. Rather, an exemplary system can predict future medical events for any given patient, regardless of how often the particular type of medical events has occurred to the patient in the past, based on how his/her longitudinal health evolves across a broad range of parameters.

In some embodiments, an exemplary system can predict an estimated risk that an individual (e.g., in a covered population) will experience a type of medical event (e.g., a future ED visit, a hospital admission, a complication). In some embodiments, the system can predict whether the medical event would be preventable. In some embodiments, the system can further predict the potential health issues or factors (e.g., an infection, a fall, a spike in blood pressure) underlying the medical event. These predictions are based on a rich set of data about the patient, his or her providers (both physicians and facilities), his or her medications and other treatments, his or her geographies and demographic characteristics (spanning outpatient and inpatient professional and facility claims, pharmacy claims, demographic and geographic and socio-economic data etc.), social determinants of health, epidemiology information (e.g., rates, incidence and characteristics of the outcomes), and also how these data are changing over time.

Embodiments of the present disclosure allow focused outreach targeting specific individuals and specific health issues and equip care coordinators with additional personalized context about the individual health needs of each member estimated to be at risk. Thus, embodiments of the present disclosure can reduce the total footprint and costs of these outreach efforts, while maintaining the effectiveness and ROI of outreach through a focus on the specific members most likely to benefit from such initiatives. Furthermore, embodiments of the present disclosure can enable health plans, ACOs, and self-insured employers to reduce the growing burden of future medical events through pre-emptive care delivery.

Embodiments of the present disclosure can be deployed in one or more client devices, one or more server devices, or a combination thereof. In some embodiments, the system comprises a software application or service accessible by healthcare personnel (e.g., a care coordinator, a nurse, a doctor) on electronic devices (e.g., a computer, a mobile device, a wearable device). In some embodiments, the system comprises one or more application programming interfaces ("API") that allows integration of the system with existing platforms (e.g., alert systems) and databases (e.g., electronic medical records or "EMR"). The system can make predictions in a scalable and real-time manner for use by care teams to improve outreach initiatives and reduce occurrence of medical events.

In some embodiments, the system can be scaled out across a variety of member populations for multiple types of medical events, including ED visits, hospital admissions, complications, and chronic disease onset, to allow for intelligent precision interception for complex populations.

As discussed above, the growing burden of the various medical events predicted by the system for patients, payers, and providers can be significantly reduced through more timely, appropriate, and cost-effective care before the medical event arises. Scaling out such patient outreach to large member populations depends critically on tools that can streamline the outreach process by focusing on specific members at elevated risk of these future medical events, as provided by embodiments of the present disclosure.

Current solutions for tackling the problem of reducing these medical events are mostly based on the notion of identifying frequent visitors (i.e., members with previous high rates of these medical events). While the number of past medical events can be correlated with future medical events, relying on this metric alone to predict cases of future medical events fails to leverage the full set of complex, longitudinal, multi-faceted information about how the unique health of each individual patient evolves. In particular, focusing on the number of past medical events alone fails to account for the substantial burden of these medical events among individuals who have not frequently had these events in the past. These cases of patients who might have infrequently had these events in the past account for a significant proportion of overall incidents of these events. Moreover, while for many patients with high rates of past medical events preventing the events might be a challenge (e.g., patients with high frailty and multiple chronic diseases), cases of these medical events among individuals who do not ordinarily have a history of them may potentially be more preventable.

Focusing exclusively on the frequency of past medical events also ignores both the member's broader set of other, different medical events in the past and important distinctions between the medical events themselves. For example, in the case of ED visits, prior encounters associated with major health crises (e.g., ED visits resulting in major surgery, hospital admission, ICU care, etc.) may represent a small proportion of ED visits, but have significantly more bearing on member health in the long-term compared to frequent ED visits because of more minor conditions. Simple metrics tracking only the number of past medical events without regard to the nature of these events and the greater context of other clinical encounters fail to take advantage of highly useful information about evolving member health while assessing future risk.

Further still, another critical challenge facing existing solutions for reducing these adverse health events is bridging the gap between predicting the risk of future medical events and enabling actions to successfully reduce this risk. Members at high risk are candidates for a variety of outreach efforts, which may range from pre-emptive scheduling of physician visits and nursing check-ups to secondary review of primary care decisions and education from care coordinators. Focusing only on the number of past medical events greatly hinders these efforts. For example, in the case of ED visits, with little to no information about the nature or causes of the predicted ED visits, outreach efforts and conversations to reduce ED visits can only be guided by high past utilization rather than anticipated future health needs. As a result, the core health issues facing these patients may often be left unaddressed by existing solutions, hindering the effectiveness of interception efforts. This is particularly important given the wide variation in the causes that may lead to future medical events; for example, most ED visits result from reasons other than the ten most common reasons for ED visits. Successfully targeting member outreach to reduce the risk of future medical events would benefit from accurate prediction of the specific reasons that might lead each member to have these events in the future.

The following description sets forth exemplary methods, parameters, and the like. It should be recognized, however, that such description is not intended as a limitation on the scope of the present disclosure but is instead provided as a description of exemplary embodiments.

Although the following description uses terms "first," "second," etc. to describe various elements, these elements should not be limited by the terms. These terms are only used to distinguish one element from another. For example, a first graphical representation could be termed a second graphical representation, and, similarly, a second graphical representation could be termed a first graphical representation, without departing from the scope of the various described embodiments. The first graphical representation and the second graphical representation are both graphical representations, but they are not the same graphical representation.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

FIGS. 1A-1C illustrate exemplary user interfaces for a system for providing personalized prediction and prevention of medical events using machine-learning algorithms, in accordance with some embodiments. In some embodiments, the user interfaces are provided via an exemplary software application or service accessible on electronic devices (e.g., a computer, a mobile device, a wearable device) by healthcare personnel (e.g., a care coordinator, a nurse, a doctor). In some embodiments, the user interfaces are integrated with existing platforms (e.g., alert systems) and databases (e.g., EMR).

The exemplary software application or service allows a user to identify and monitor at-risk patients, as well as initiating and tracking interactions with the patients. The user can be healthcare personnel, such as care coordinators, nurses, doctors, population health managers, actuaries, and administrators. The software application or service can be used for (1) predictive outreach and care/outcome improvement, (2) predicting future utilization for planning purposes, (3) evaluating quality/outcomes and understanding populations, among other things.

With reference to FIG. 1A, the user interface 100 provides a plurality of user affordances 102-110 for providing interception data for various types of medical events including "Emergency Department Visits," "Inpatient Admissions," "Utilization Escalation," "Chronic Disease Complication," and "Chronic Disease Onset." In some embodiments, the user interface 100 is displayed when the user provides login credentials. In some embodiments, the types of medical events displayed on the user interface 100 are tailored based on the role of the user.

With reference to FIG. 1B, user interface 120 is displayed upon a user selection of user affordance 102 (FIG. 1A). The user interface displays a list of patients (e.g., "Andrea Adams," "Robert Anderson") in the user's organization. For each patient, the user interface provides associated information, such as member ID, a risk value, an interceptability value, and the assigned healthcare individual.

The risk value indicates how a particular patient is at risk for a type of medical event. In the depicted example, the risk value is on a scale of 1 to 5. For example, for "Andrea Adams," the risk of having a future ED visit with a certain time period (e.g., 6 months) is indicated to be high. The risk value can be obtained based on the patient's health parameters and one or more machine-learning algorithms, as described below.

The interceptability value indicates how likely a future medical event can be prevented or intercepted. In the depicted example, the interceptability value is on a scale of 1 to 3. For example, for "Andrea Adams," the likelihood that a future medical event can be prevented is indicated to be high. The interceptability value can be obtained based on the patient's health parameters and one or more machine-learning algorithms, as described below.

In the depicted example, the patient "Andrea Adams" has a high risk of making a future ED visit and a high likelihood that the future ED visit can be prevented. Accordingly, the risk value and the interceptability value indicate to a care coordinator that Andrea is a candidate for outreach efforts.

The user interface 120 further comprises a menu 122 comprising a plurality of filters that can be applied to the list of patients. As shown in FIG. 1B, the menu can be used to filter the list of patients by state, by plan type, by review status, and by interceptability. Further, the user interface 102 comprises multiple tabs 124 such that the user can view patients based on the assignment status.

With reference to FIG. 1C, when the user selects a patient in the list of patients in the user interface 120 (e.g., via a touch input, via a mouse click), a pop-up 130 is displayed. The pop-up includes detailed information about the selected patient, including the risk value, the intercepability value, the assignment status, the clinical risk factor, the number of prior ED visits, the plan type, and the review status.

The clinical risk factor indicates the predicted underlying reason for the future medical event. In the depicted example, the patient "Brad Brandt" is indicated to have a high risk of making a future ED visit and the predicted underlying reason for the future ED visit is "cough." The clinical risk factor can be generated by the patient's health parameters and one or more machine-learning algorithms, as described below. In some embodiments, the software application or service can provide a predicted cost associated with the future ED visit.

In some embodiments, the software application or service allows the user to contact a patient from the application via email, text, phone call, or a combination thereof. The application or service can track a history of attempted contacts and their results. The user can also add notes to a patient's case and tag other users in the notes (e.g., for review, for assignment). In some embodiments, the software application or service can automatically track status of patient cases, including new/unread (i.e., new cases unseen by the user), read (i.e., the user has clicked on the case and viewed it, but no interaction with the patient), in progress (i.e., communication with patient is currently in progress), complete (i.e., patient was successfully contacted).

With reference to FIG. 1C, the user can assign the patient to herself using the pop-up. In some embodiments, the user can batch-assign patient cases to herself. For example, the user can filter for all cardiac patients in New Jersey Medicaid plan, and assign all those cases to herself.

Figure 1D:
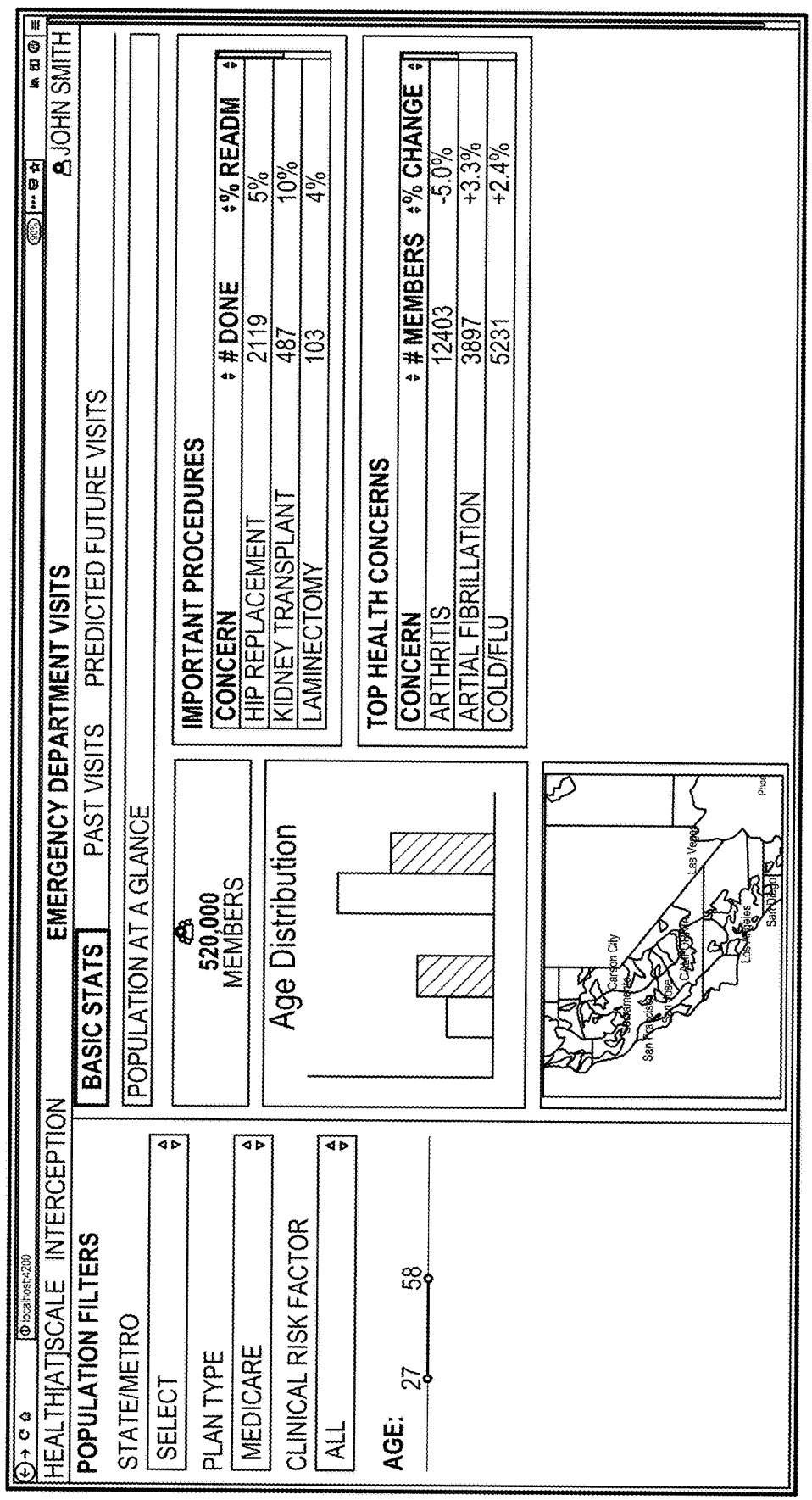
FIG. 1D illustrates an exemplary user interface of a system for providing personalized prediction and prevention of various types of medical events, in accordance with some embodiments.
Figure 1E:
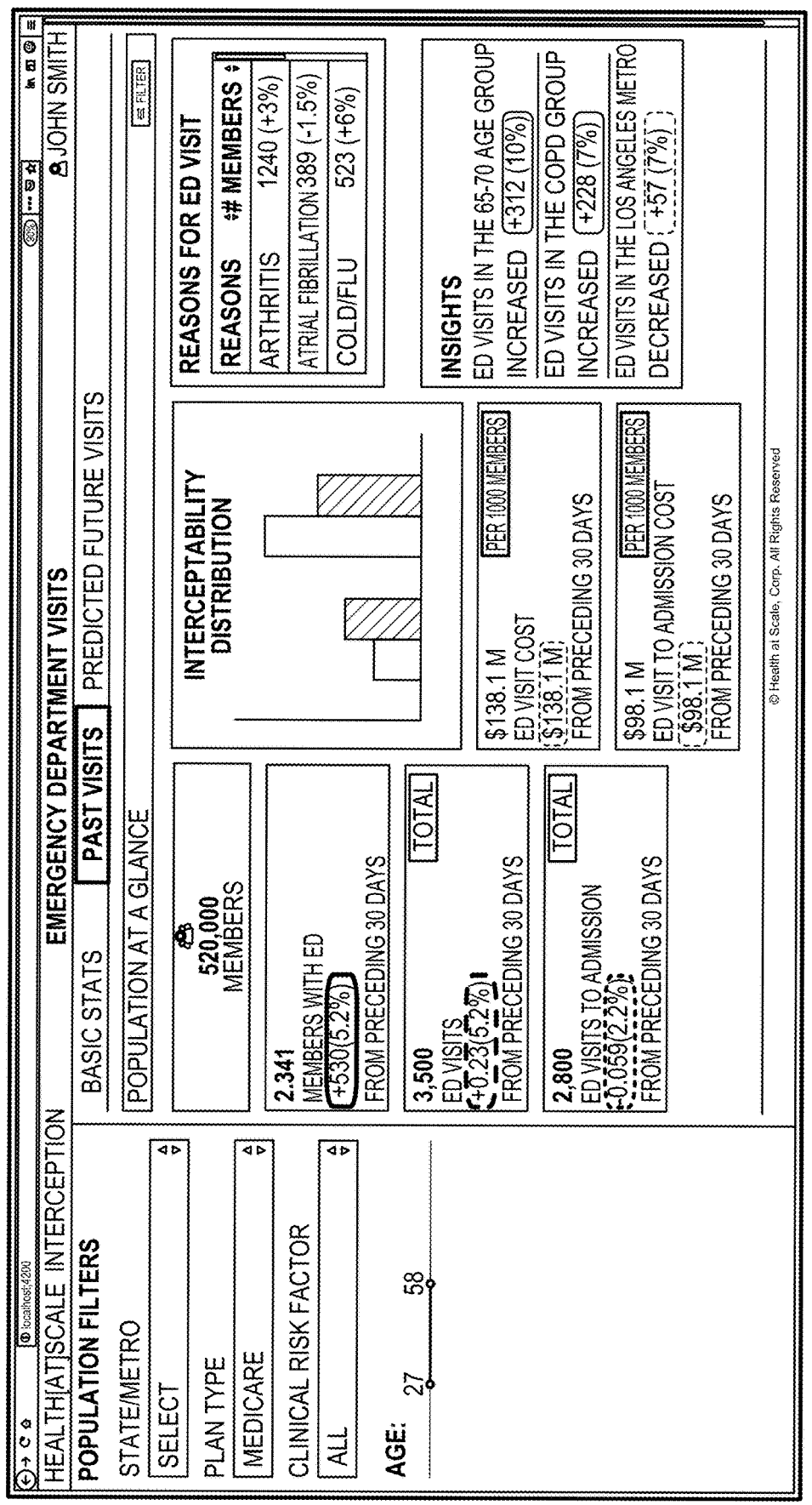
FIG. 1E illustrates an exemplary user interface of a system for providing personalized prediction and prevention of various types of medical events, in accordance with some embodiments.
Figure 1F:
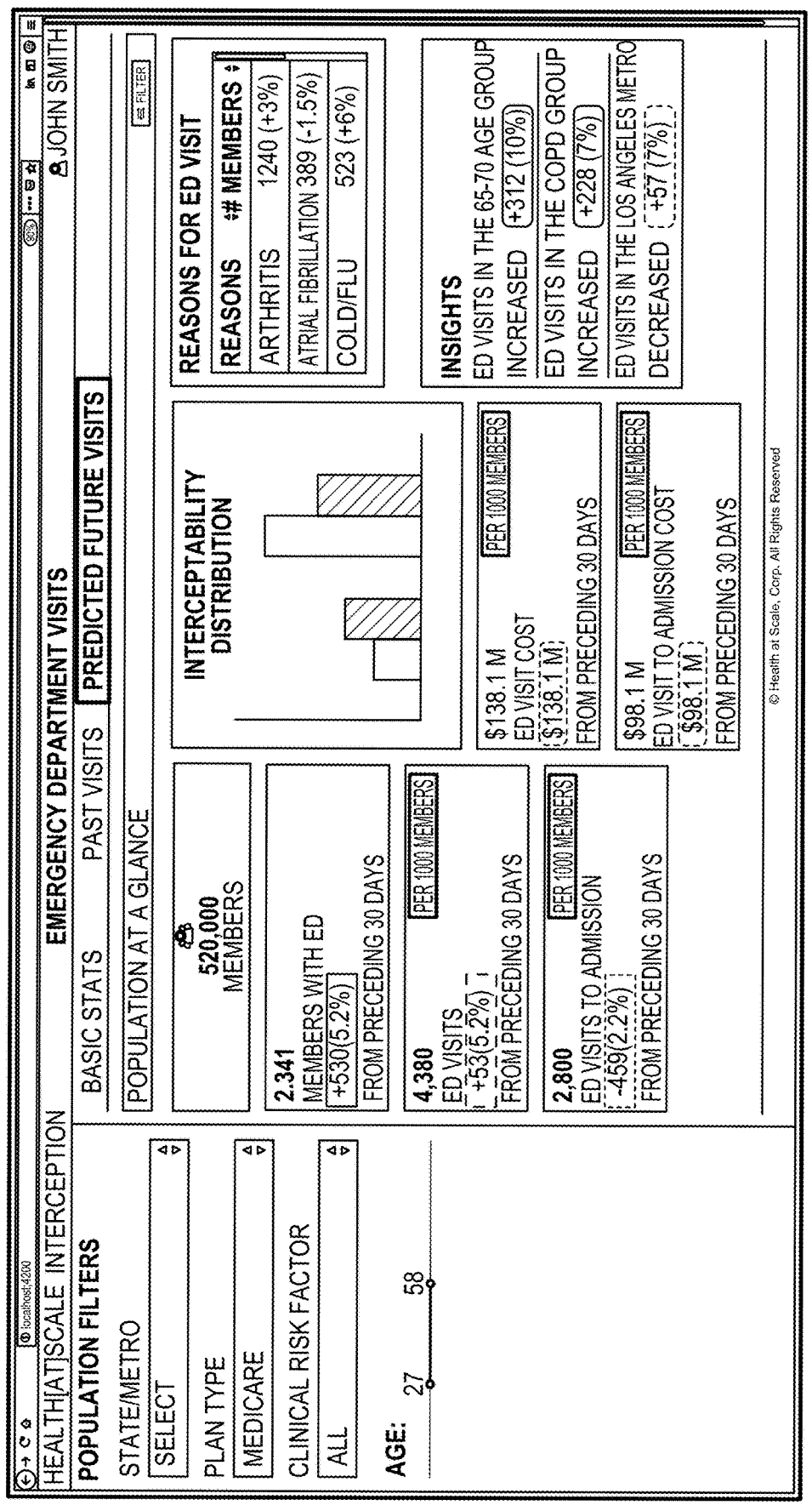
FIG. 1F illustrates an exemplary user interface of a system for providing personalized prediction and prevention of various types of medical events, in accordance with some embodiments.

In some embodiments, the software application or service can offer an overview of predicted events in a population and how they are distributed (e.g., across lines of businesses, geographies). This population-level dashboard allows users to get a quick understanding of an entire population at a glance. FIGS. 1D-F illustrate exemplary views of a population-level dashboard, in accordance with some embodiments. As depicted, the dashboard can allow a user to specify a particular population (e.g., by location, age, and medical plan).

In some embodiments, the main dashboard page is a page of basic statistics on the population, including information about the number of members, the age distribution, and the geographic distribution. It can further include information about important procedures performed in the population, along with number of times the procedure was performed, the associated costs, readmission rates, complication rates, deltas in those numbers from one time period to the next, etc. It can further include similar information about the diagnoses and comorbidities of the population, listing information such as the number and percentage of people affected, the associated costs, deltas in those numbers from one time period to the next, etc.

The population-level dashboard also contains detailed views of statistics for each predicted health event of interest (e.g., ED visit, hospital admission, etc.). A detailed view allows users to choose a time frame, either in the past or the future. For example, users can choose "the past 30 days" as a time frame, or "the next 90 days" as a time frame. The page shows statistics calculated with respect to that time frame, including the number of members with the health event, the associated costs, distributions of the reasons for the health events, and deltas in those numbers from the preceding time frame to the current one of interest. It also gives insights on trends and sub-populations that are noteworthy. For example, if a specific geography or a population with a specific comorbidity is predicted to show an increase in risk, or an increase in a particular diagnostic reason for a health event, the page would show that information. If the time frame is in the past, the statistics can be calculated using the past data.

If the time frame is in the future, the statistics are calculated using the output of the models described below. For example, to display statistics on the number of members with ED visit in a future time frame, the model that predicts risk of ED visit would be run to generate a probability of ED visit for each member, and an expected value would be calculated accordingly. Similarly, to display statistics on the distribution of reasons for those visit, the model that predicts reason would be run on all members, and an expected value would be calculated by averaging those per-member distributions, weighted by the likelihood that each member has an ED visit. All of these pages described can be filtered to subpopulations of interest, such as filtering by geography, plan type, clinical risk factor, age, etc.

Figure 2A:
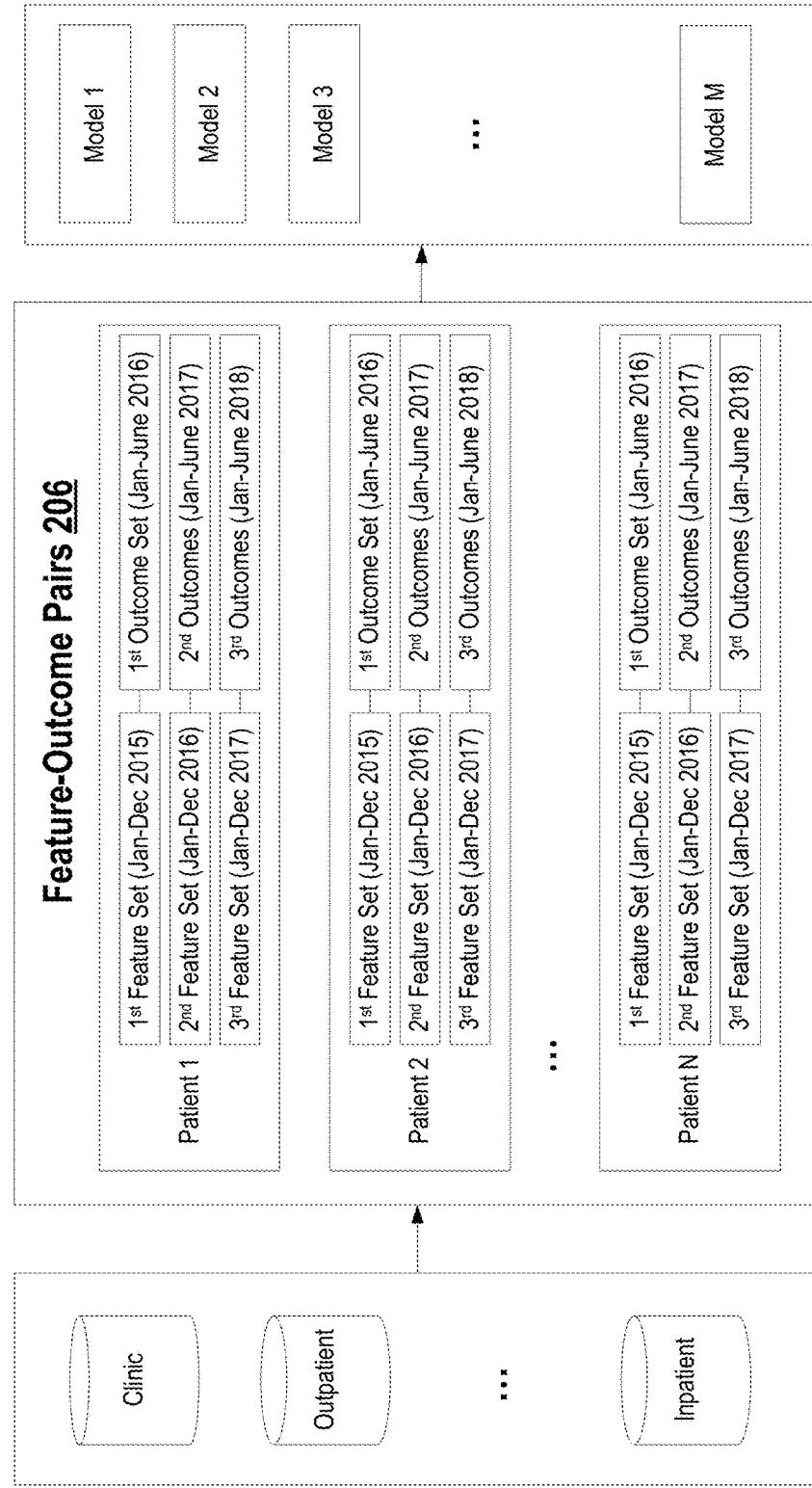
FIG. 2A illustrates an exemplary system for providing personalized prediction and prevention of various types of medical events, in accordance with some embodiments.

FIG. 2A depicts an exemplary system 200 for providing personalized prediction and prevention of medical events (e.g., ED visits) using machine-learning algorithms, in accordance with some embodiments.

With reference to FIG. 2A, the exemplary system 200 (e.g., one or more electronic devices) obtains data 202. The data 202 can be related to one or more patients. In some embodiments, the data 202 include biometric data, social and/or demographical data, medical claims data, clinical data, inpatient data (e.g., data from hospital admissions, including length of stay, reasons for the admission, procedures conducted during the admission, etc.), outpatient data (e.g., data from ED visits which did not lead to hospital admission, outpatient surgeries and procedures, etc.), facility data (e.g., data from hospitals, ambulatory surgical centers, skilled nursing facilities, home health agencies, etc.), professional data (e.g., data from encounters with physicians, including PCP visits, specialist consultations, etc.), pharmacy data, enrollment data (e.g., data about which healthcare plans a patient was enrolled in, and dates of these enrollments), data related to epidemiology (e.g., the incidence, prevalence, frequency etc. of events), or any combination thereof. In some embodiments, the data 202 can be obtained (e.g., pulled periodically from, requested from) a plurality of data sources, such as databases of care providers, insurance providers, third-party knowledge repositories, wearable devices, or any combination thereof.

In some embodiments, the system applies one or more preprocessing algorithms on the data 202. For example, the system can identify and remove errors and inconsistencies from the data 202. As another example, the system can remove duplications and merge data as necessary. As another example, the system can create associations between portions of data 202 and assign annotations and/or attributes to the data 202.

The system obtains patient-specific data 204 based on the data 202. The patient-specific data comprises one or more datasets corresponding to the one or more patients, respectively. In the depicted embodiment, each dataset for a patient includes a plurality of feature-outcome pairs 206 for the respective patient.

With reference to FIG. 2A, the dataset for "Patient 1" comprises a plurality of (e.g., 3) feature-outcome pairs. The first feature-outcome pair comprises a feature set corresponding to a first predefined time period (e.g., "January-December 2015") and an outcome set corresponding to second predefined time period (e.g., "January-June 2016"). FIG. 2B illustrates an exemplary feature-outcome pair, which comprises a feature set and an associated outcome set for a patient, as described in detail below.

In the depicted embodiment, the first predefined time period is a one-year time period, and the second time period is a six-month period following the first predefined time period. In some embodiments, the first time period and the second time period are adjustable. For example, the first time period can be set to 3 months, 6 months, 1 year, 2 years, etc. As another example, the second time period can be set to 3 months, 6 months, 1 year, 2 years, etc. The first time period can precede the second time period by some time, or immediately precede the second time period.

Similarly, the second feature-outcome pair for "Patient 1" comprises a feature set corresponding to "January-December 2016" and an outcome set corresponding to "January- June 2017." The third feature-outcome pair for "Patient 1" comprises a feature set corresponding to "January-December 2017" and an outcome set corresponding to "January-June 2018."

In the depicted embodiment, for "Patient 1," the first feature set is associated with a year (i.e., "January-December 2015") immediately preceding the year of the second feature set (i.e., "January-December 2016"); further, the second feature set is associated with year preceding the year of the third feature set (i.e., "January-December 2017"). In some embodiments, the first, second, and third feature sets are associated with a sliding window of a predefined size (e.g., 1 year) with a predefined hop size (e.g., 3 months). For example, the first feature set and the second feature set can be associated with "January-December 2015" and "April 2015-April 2016," respectively.

Each feature set comprises a plurality of features. In some embodiments, for each feature, the system obtains a single feature value. The feature value can be a scalar value, a vector, a matrix, or a combination thereof. For example, if the plurality of features includes 50 features, the system obtains 50 feature values for the first feature set for Patient 1. Further, each feature value for the first feature set is calculated based on data associated with the time period "January-December 2015."

The feature value can be a number (e.g., binary, integer), a vector, a matrix, or a combination thereof. In some embodiments, the feature value can be a derived value based on multiple values, such as a standard deviation, an average, a trend/distribution of multiple values. In some embodiments, the feature can be based on a predefined rule (e.g., the value may be indicative of whether a predefined threshold is met).

In some embodiments, the plurality of features comprises demographic information of a patient, such as age, gender, and race. For example, an exemplary feature value can be the age of the patient. As another example, a feature value can be the age bracket the patient belongs to.

In some embodiments, the plurality of features comprises comorbidities or existing chronic diseases of the patient. For example, an exemplary feature value can be a vector corresponding to a plurality of conditions, with a binary value indicating the presence of each condition.

In some embodiments, the plurality of features comprises past medical history, such as past diagnoses and procedures, of the patient. In some embodiments, past diagnoses and/or procedures are defined by ICDs, CPTs, LOINCs, DRGs, CCS, Revenue Codes etc. For example, an exemplary feature value can be a vector corresponding to a plurality of diagnoses as defined by ICD-10 codes, with a binary value indicating the presence of each condition. As another example, an exemplary feature vector can be a vector listing a plurality of diagnoses attributable to the patient, in which each diagnosis is represented by its ICD-10 code.

In some embodiments, the plurality of features comprises information regarding care providers of the patient. The information can be, for example, distance to the patient's nearest hospitals and/or nearest urgent care clinics. The information can be wait time at nearest hospitals and/or at nearest urgent care clinics.

In some embodiments, the plurality of features comprises whether or not the patient has a primary care physician.

In some embodiments, the plurality of features comprises the number of past medical events (e.g., ED visits) by the patient.

In some embodiments, the plurality of features comprises diagnoses of past medical events (e.g., ED visits) by the patient.

In some embodiments, the plurality of features comprises prior utilization by the patient (e.g., charges and costs for earlier medical events and encounters.).

In some embodiments, the plurality of features comprises discharge statuses of any inpatient stays by the patient.

In some embodiments, the plurality of features comprises prior utilization of medical encounters by the patient. For example, the features could include the number of prior hospitalizations, prior emergent and non-emergent outpatient encounters, prior procedures performed, prior physician visits, etc.

In some embodiments, the plurality of features comprises which physician specialties the patient has seen.

In some embodiments, the plurality of features comprises which facility types (e.g., hospital, women's clinic, mental health clinic) the patient has visited.

In some embodiments, the plurality of features comprises which medical events (e.g., ED visits) led to hospital admission by the patient and associated reasons.

In some embodiments, the plurality of features comprises the number and diagnoses/procedures of inpatient admissions by the patient.

In some embodiments, the plurality of features comprises lengths of inpatient admissions by the patient.

In some embodiments, the plurality of features comprises the number and diagnoses and/or procedures of clinic visits.

In some embodiments, the plurality of features comprises the medications the patient is on or has been on in the past In some embodiments, the plurality of features comprises medical chart information (e.g., most recent heart rates, blood pressures).

In some embodiments, the plurality of features comprises health habits (e.g., frequency of smoking, drinking, exercise) of the patient.

In some embodiments, the plurality of features comprises family medical history, for example, which chronic diseases family members of the patient have and which family members have these diseases.

In some embodiments, the plurality of features comprises data from wearable devices of the patient. In some embodiments, the plurality of features comprises lab tests and imaging tests and the results for these tests.

In some embodiments, the plurality of features comprises data from other telemetric devices (e.g., weight scales) of the patient.

In some embodiments, the plurality of features comprises social determinants of health of the patient (e.g., patient education levels, occupation status, income levels).

In some embodiments, the plurality of features comprises how often other patients who went to the same physicians seen by the patient had subsequent ED visits. For example, the system can calculate, for each physician, the rate (e.g., proportion, percentage) of patients they saw who had an ED visit 3 months, 6 months, and 12 months following the visit to the physician. Then, for each patient, the system obtains the ED rates for all the physicians the patient visited. In some embodiments, the plurality of features includes the minimum, the median, the mean, and/or the maximum of these ED rates.

In some embodiments, for a feature that is a vector with a relatively high dimensionality (e.g., procedures the patient has had, as represented by the first three digits of the ICD procedure code), the system can reduce the dimensionality of the vector by including only those procedures exceeding a predefined frequency threshold in the data.

In some embodiments, the system can reduce the dimensionality of the vector by using a specific taxonomy of diagnoses. The specific taxonomy can include hierarchical classes by medical similarity.

In some embodiments, the system can use the approach of replacing these features with alternative measures based on their descriptions. For example, in one implementation, the system creates a set of all meaningful words in the textual descriptions of these features and converts each feature into a binary vector where each element of the vector represents whether or not the textual description of that feature contains a specific word. Specifically, in the case of diagnoses, the vector might have elements that represent words like "infection", "respiratory", or "chronic", so each specific diagnosis is represented by a binary vector that defines which of those words is contained in its textual description.

In some embodiments, the system can use vector embeddings for the diagnoses and procedures. For example, the system can use mappings from ICDs/CPTs to vectors which represent the diagnosis/procedure numerically. The embedding can be taken as pre-trained embeddings, but we can also train these embeddings ourselves on our dataset. These embeddings are created by training in a manner similar to that in which words are given embeddings through word2vec with the difference being that words are replaced with ICD/CPT codes, and instead of a word's context being defined by those words surrounding it within sentence, a code's context is defined by the codes that surround it temporally for a given patient or encounter. In some embodiments, other embedding approaches can also be based on neural networks, factorization, probabilistic models and other approaches.

With reference to FIG. 2A, each feature set is associated with a corresponding outcome set for a patient. The outcome set comprises a plurality of outcome values. In the depicted example, each outcome value in the first outcome set is calculated based on data associated with the time period "January-June 2016."

In some embodiments, the plurality of outcomes includes whether or not the patient has had a particular type of medical event (e.g., an ED visit, a hospital admission, developed a new chronic disease). In some embodiments, the plurality of outcomes includes a first binary value indicating whether the patient has had the medical event during a first time period (e.g., 3 months), a second binary value indicating whether the patient has had the medical event during a second time period (e.g., 6 months), a third binary value indicating whether the patient has had the medical event during a third time period (e.g., 9 months), etc. In some embodiments, the plurality of outcomes includes a first scalar value indicating the number of medical event instances (e.g., the number of ED visits) during a first time period (e.g., 3 months), a second scalar value indicating the number of medical event instances during a second time period (e.g., 6 months), a third scalar value indicating the number of medical event instances (e.g., the number of ED visits) during a third time period (e.g., 9 months), etc. In some embodiments, outcomes can also be time to events, with the associated models predicting the times at which events can be expected to occur or the hazard for these events as a function of time.

In some embodiments, the plurality of outcomes includes the reason that the medical event occurred (e.g., why the patient visited the ED, why the patient was admitted to the hospital, what chronic disease occurred). The reason can be automatically obtained from medical records (e.g., a diagnosis, the patient's description of symptoms). In some embodiments, the reason is indicated by the applicable diagnosis class (e.g., as defined by ICD codes or specific taxonomy). In some embodiments, multiple reasons can be included in the plurality of outcomes. For example, the outcome value can be a vector including a predefined number of primary reasons for the medical event. As another example, the outcome value can be a vector including reasons for first and last medical events. As another example, the outcome value can be a matrix including the reasons and the associated probabilities. As another examples, the multiple reasons can be grouped into clusters, and the outcome value can be a vector including these clusters.

In some embodiments, the plurality of outcomes includes additional outcome characteristics. For example, when the medical event is an ED visit, the plurality of outcomes includes whether or not the ED visit led to hospital admission. As another example, when the medical event is an ED visit or hospital admission, the plurality of outcomes includes the costs of the medical events.

In some embodiments, the plurality of outcomes includes percent change in utilization, absolute change in utilization, whether or not these changes were above a certain threshold, and the main health issue driving the utilization increase.

It should be appreciated that the above-described outcomes are merely exemplary. Any metric that can provide insight into a patient's future health conditions can be included in the outcome set, then used to train one or more machine-learning algorithms, and then provided via the user interfaces described with reference to FIGS. 1A-C.

Patient-specific data 204 is used to train a set of machine-learning models 210. In some embodiments, the set of machine-learning models comprises a single model for predicting multiple metrics of multiple medical events (e.g., a single neural network). In some embodiments, the set of machine-learning models comprises multiple models corresponding to multiple medical events (e.g., a single model for predicting metrics for ED visits, a single model for predicting metrics for hospital admissions). In some embodiments, the set of machine-learning models comprises multiple models corresponding to multiple metrics (e.g., a single model for predicting a likelihood of a future ED visit, a single model for predicting a likelihood of a reason for the future ED visit, a single model for predicting a likelihood that the future ED visit can be prevented, respectively). While descriptions below are provided with reference to a set of models each corresponding to a specific metric and a specific medical event, it should be appreciated that they are equally applicable when the set of models comprises a different combination of models or a single model.

Figure 2C:
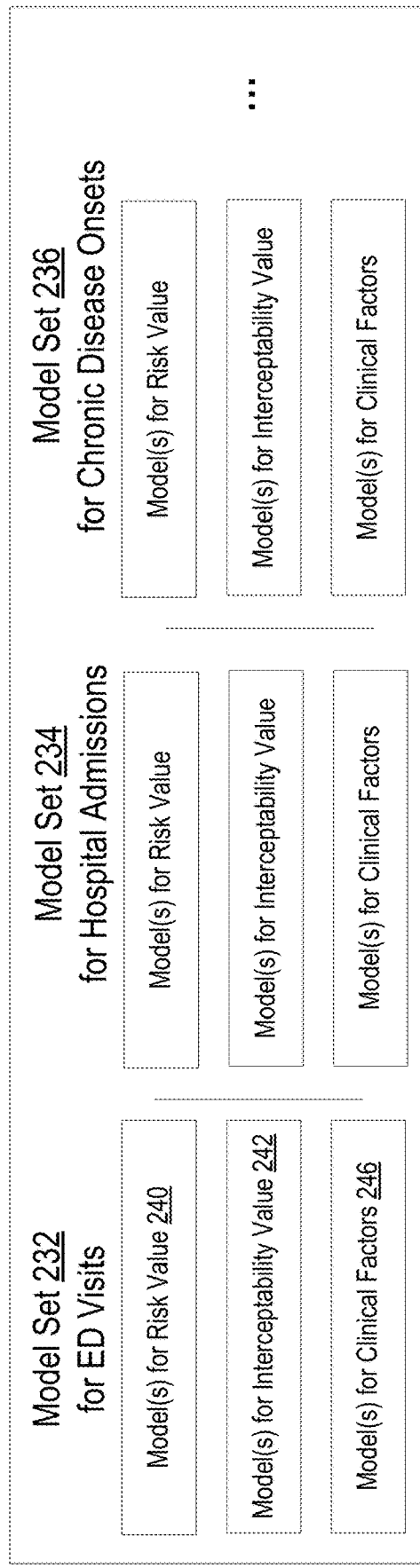
FIG. 2C illustrates an exemplary plurality of machine-learning models, in accordance with some embodiments.

An exemplary plurality of machine-learning models are depicted in FIG. 2C. As shown in FIG. 2C, the plurality of models 230 comprises multiple model sets corresponding to multiple types of medical events, respectively. For example, the plurality of models 230 comprises a model set 232 for predicting ED visits, a model set 234 for predicting hospital admissions, and a model set 236 for predicting chronic disease onsets. Additional model sets can be included for predicting utilization escalations, chronic disease complications, etc.

Each model set comprises one or more models for obtaining a risk value for a medical event (e.g., model(s) 240 for predicting whether an ED visit will occur), one or more models for obtaining an interceptability value for the medical event (e.g., model(s) 242 for predicting whether the ED visit is preventable), one or more models for obtaining clinical factors underlying the medical event (e.g., model(s) 246 for predicting clinical factors underlying the ED visit). It should be appreciated that additional models can be included in the model set for predicting additional outcome characteristics of the medical event (e.g., whether a hospital admission will occur after the ED visit, outcomes for a different time period length).

Each model can be trained to receive a set of feature values for a patient and output a predicted outcome for the patient, as described below.

In some embodiments, a model of model(s) 232 is trained to receive a set of feature values and output a probabilistic value indicating whether the patient is likely to make an ED visit in a specific time period (e.g., 6 months). The model can be trained using feature sets (e.g., some or all of feature sets for patients 1-N in FIG. 2A) and the corresponding outcome values (e.g., binary values indicating whether these patients had an ED visit in the subsequent 6-month period) in the outcome sets. In some embodiments, the model 232 is a neural network model, a logistic regression model, an ensemble model, or any one of a variety of other regression or classification models, such as random forest, support vector machine, naive Bayes, nearest neighbors, linear regression, etc. In some embodiments, the model 232 is a binary model.

During the inference stage, a plurality of features of a particular patient (e.g., feature values of Andrea Adams between January-December 2019) are inputted into the model(s) 232 to obtain a probabilistic value (e.g., a prediction of whether Andrea Adams will have an ED visit between January-June 2020). The system can further obtain a risk value (e.g., on a scale of 1 to 3) based on the probabilistic value. In some embodiments, the system obtains the risk value based on a rule (e.g., 0-0.3 corresponds to a risk value of 1). In some embodiments, the system trains another machine-learning model (e.g., a regression model) that is configured to receive a probabilistic value and output a risk value.

In some embodiments, a model of model(s) 246 is trained to receive a set of feature values and output clinical factors underlying the ED visit. During training, feature sets (e.g., some or all of feature sets for patients 1-N in FIG. 2A) and the corresponding outcome values (e.g., clinical factors) in the outcome sets are used to train the model 246. In some embodiments, the model 246 is a neural network model, an ensemble model, or any one of a variety of other regression or classification models, such as random forest, support vector machine, naive bayes, nearest neighbors, linear regression, etc. In some embodiments, the model 246 is a multiclass model.

In some embodiments, the model 246 is trained to output probabilistic values associated with a plurality of reasons for the medical event (e.g., pneumonia, arrhythmia, urinary tract infection, bipolar disorder).

During the inference stage, a plurality of features of a particular patient (e.g., feature values of Andrea Adams between January-December 2019) are inputted into the model(s) 246 to obtain probabilistic values associated with a plurality of reasons for the medical event (e.g., a prediction of why Andrea Adams will have an ED visit between January-June 2020). The system then outputs the top reasons based on these probabilistic values, potentially omitting reasons whose associated probabilities are below a specific threshold. In some embodiments, the thresholds are different for each ranking of reason (e.g., the top most likely reason has a threshold that is lower than the second most likely reason) so that the system is more likely to output at least one reason, and only outputs additional reasons if the system is more confident in their likelihoods.

In some embodiments, the model 246 comprises multiple models. Specifically, a first model is trained to predict a high-level reason for the medical event (e.g., one reason out of a small number of diagnosis classes including classes such as "respiratory" and "cardiovascular"). For each diagnosis class (e.g., "cardiovascular"), a secondary model is trained based on only data associated with patients who visited ED for that diagnosis class (e.g., data associated with patients that visited ED for cardiovascular reasons) to predict the precise reason.

During the inference stage, a plurality of features of a particular patient (e.g., feature values of Andrea Adams between January-December 2019) are inputted into the model(s) 246 to obtain probabilistic values associated with a plurality of high-level reasons for the medical event. Based on the high-level reason associated with the highest probabilistic value, the system selects the corresponding secondary model to predict the precise reason.

In some embodiments, the system first trains model(s) 240 and then trains model(s) 246 such that the training of the model(s) 246 can be focused on patients at elevated risk. For example, after the model(s) 240 is trained, the system can then train model(s) 246 where the training data corresponding to various patients can be weighted by the predicted risk values of these patients, thus guiding the model(s) 246 to prioritize the types of patients on which it will be predicting during the inference stage.

In some embodiments, a model of model(s) 242 is trained to receive a set of feature values and output a probabilistic value indicating whether the ED visit is preventable. During training, the model is trained based on feature sets (e.g., some or all of feature sets for patients 1-N in FIG. 2A) of patients that have been outreached and the corresponding outcome values (e.g., whether an ED visit was still made) in the outcome sets. In some embodiments, the model 234 is a neural network model, a logistic regression model, an ensemble model, or any one of a variety of other regression or classification models, such as random forest, support vector machine, naive bayes, nearest neighbors, linear regression, etc. In some embodiments, the model 234 is a binary model.

During the inference stage, a plurality of features of a particular patient (e.g., feature values of Andrea Adams between January-December 2019) are inputted into the model(s) 242 to obtain a probabilistic value indicating whether an ED visit would be preventable for that patient. The system can further obtain an intercepability value (e.g., on a scale of 1 to 5) based on the probabilistic value. In some embodiments, the system obtains the intercepability value based on a rule (e.g., 0-0.2 corresponds to an intercepability value of 1). In some embodiments, the system trains another machine-learning model (e.g., a regression model) that is configured to receive a probabilistic value and output an intercepability value.

Figure 3:
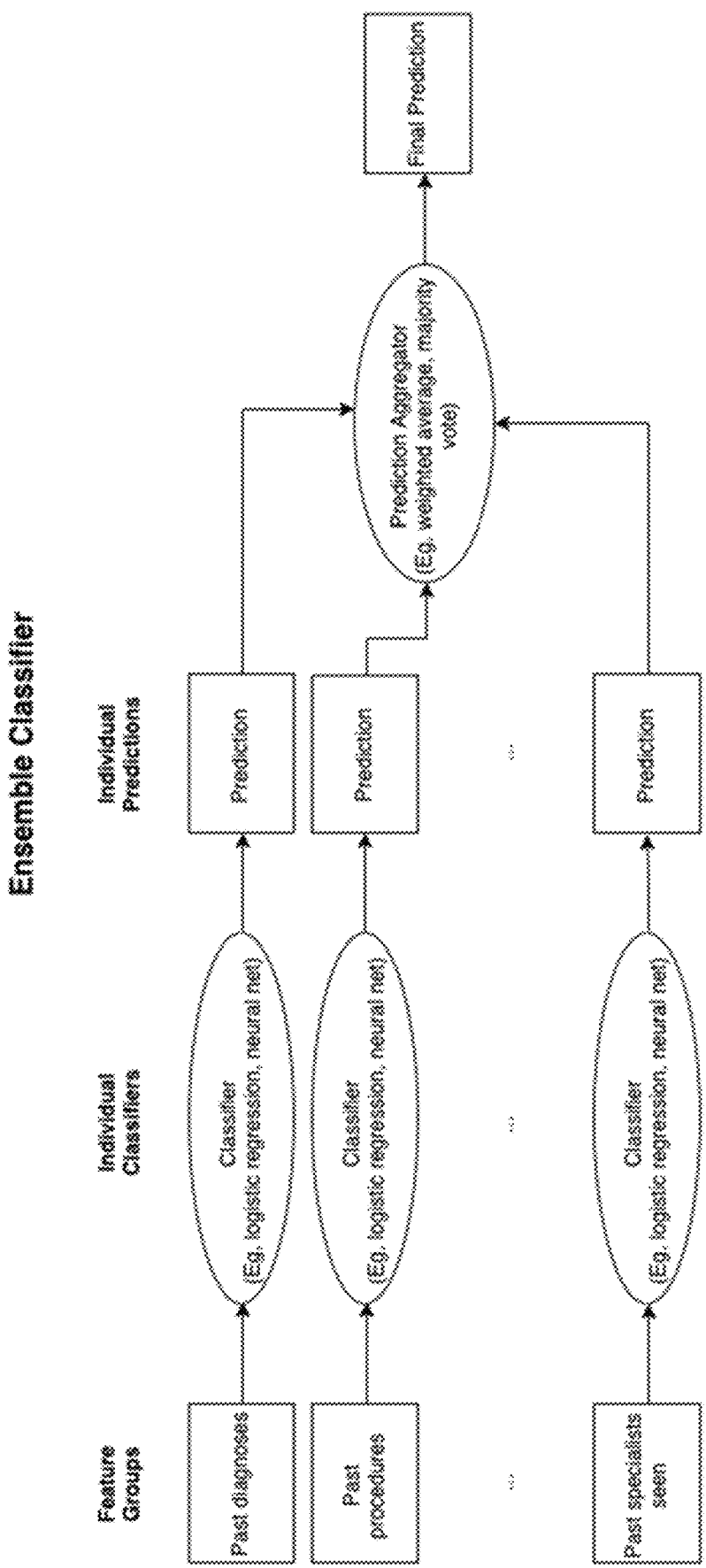
FIG. 3 illustrates an exemplary ensemble model, in accordance with some embodiments.

In some embodiments, one or more models of the plurality of models 230 are ensemble models. For each ensemble, the system trains multiple machine learning classifiers, and combines their outputs to produce one final output prediction. With reference to FIG. 3, each machine learning classifier is trained with a different group of features. For example, a first classifier can be trained using features related to past diagnoses to predict a specific outcome (e.g., whether the patient will have an ED visit); a second classifier can be trained with features related to past procedures to predict the same outcome. Each of these classifiers will output a prediction in the form of a number.

As shown in FIG. 3, these predictions are then aggregated to provide an output prediction. The aggregation can be one of several different methods. Examples of aggregation methods include taking a majority vote of the binarized outputs, or taking a weighted average of the continuous outputs (e.g., if outputs represent probability of risk).

If the aggregation method is a weighted average, the weights can be uniform (i.e., each model gets the same weight), or weights can be determined by factors such as the performance of the models, with better-performing models receiving greater weight. The ensemble approach above can be implemented using a deep learning approach (where there are hierarchical naturally layers inherent to the model) or by using other classifiers that are organized in a hierarchical manner. The ensemble approach allows for a combination of different types of machine-learning models, which may be suited for learning different tasks. Further, the ensemble approach provides a more nuanced and granular prediction of the outcome.

Figure 4:
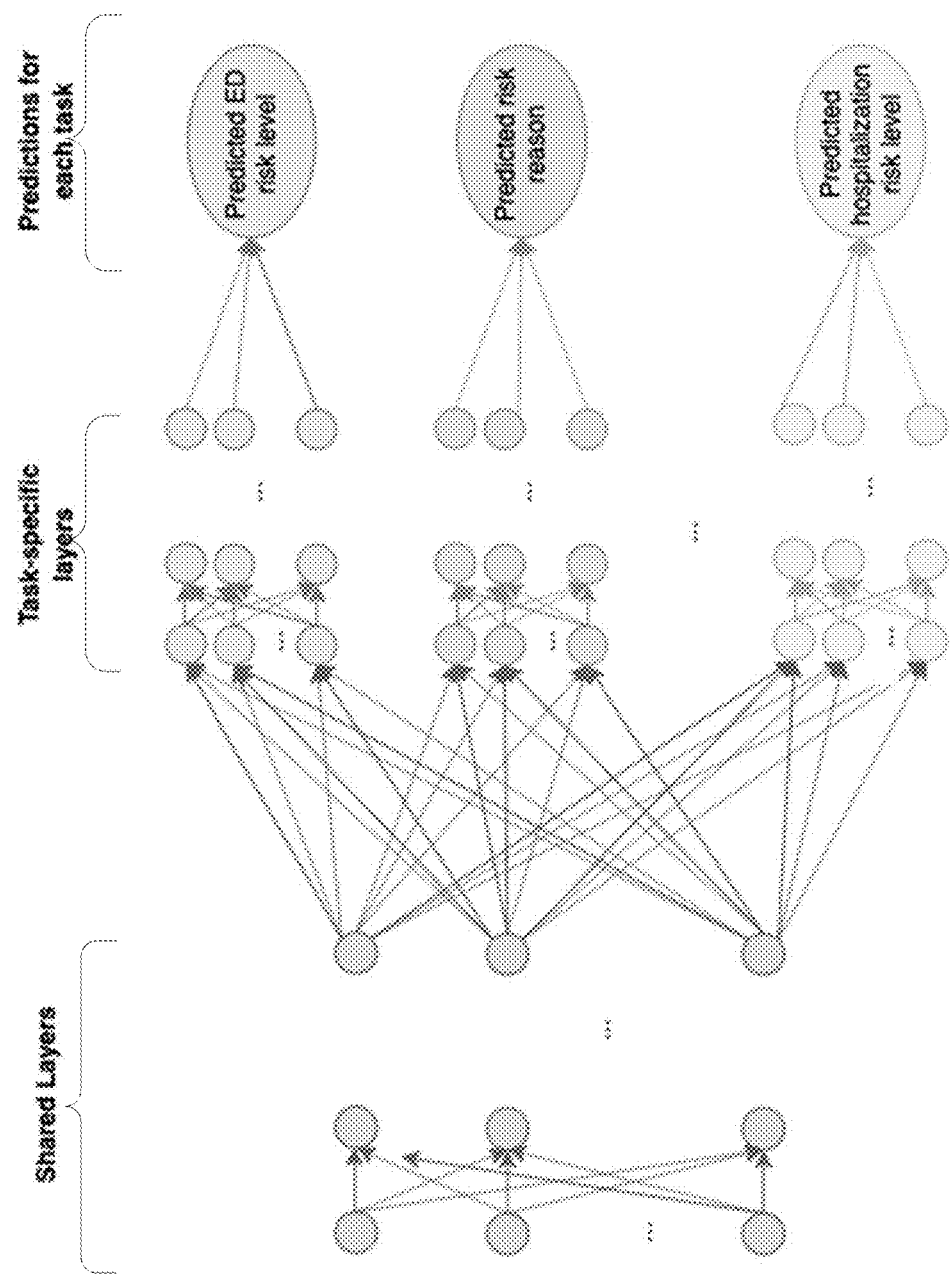
FIG. 4 illustrates an exemplary multi-task learning model, in accordance with some embodiments.

In some embodiments, one or more models of the plurality of models 230 are multi-task learning models. This approach takes advantage of commonalities in solving different machine learning tasks. In some embodiments, some (e.g., models for predicting risk values of various medical events) or all of models 230 are neural networks with initial shared architecture, as shown in FIG. 4. The shared layers of the network allow common processing to be performed on the input features, and then the task-specific layers take in those processed features to produce the output for each task.

In some embodiments, models configured to predict the same outcome (e.g., classifiers in an ensemble model in FIG. 3) can be trained via multi-task learning. In some embodiments, models configured to predict different outcomes (e.g., models for predicting risk values of ED visits, hospital admissions, and complications) can be trained via multi-task learning to synergistically improve model training and share state between the model training in a way that benefits all models and improves their training from what would have been possible if each outcome was modeled individually. In some embodiments, the multi-task learning can be implemented through task parameter coupling or through shared subspace discovery etc.

In some embodiments, the system trains a first plurality of models (e.g., 230) for a first type of patients, a second plurality of models for a second type of patients, etc. In some embodiments, the types of patient are based on past utilization rate. For example, the system trains a first plurality of models for patients with no past ED visits, a second plurality of models for those with 1-3 past visits, and a third plurality of models for those with 4+ past visits. During the inference stage, the system can first determine a patient's past utilization, and then select the corresponding models to obtain predictions for the patients.

In some embodiments, when predicting risk for relatively rare events (e.g., predicting risk for an ED visit with a specific diagnosis), the system can perform undersampling of the common class (e.g. the negative class when predicting risk of ED visit for a fall) by taking all the samples with positive label, and sampling randomly a roughly equal number of samples with negative label. In another setting, the system can oversample the less frequent class (using methods such as SMOTE; synthetic minority oversample technique). In yet other embodiments, the system can use cost-sensitive weighting to over-weight less common examples. In still other embodiments, the system can use 1.5 class learning approaches that combine classification with anomaly detection for imbalanced data.

In some embodiments, the system filters out, from the training data, any data in a feature-outcome pair if the patient was not enrolled full-time in a healthcare system during the period when the feature set and the outcome set are taken (e.g., a 18-month period in FIG. 2).

In some embodiments, training data is weighted by recency. Thus, the models prioritize learning based on medical events that are more recent.

In some embodiments, the system can use optimization error metrics that optimize univariate and multi-variate loss.

Turning back to FIG. 2C, after the models 230 are trained, the trained models can be used to obtain risk values, intercepability values, and clinical factors for new patients during the inference stage. The predictions can be displayed via user interfaces described with reference to FIGS. 1A-C.

For example, a plurality of features of a new patient (e.g., feature values of Andrea Adams between January-December 2019) can be inputted into the model(s) 232 to obtain a probabilistic value (e.g., a prediction of whether Andrea Adams will have an ED visit between January-June 2020). The system can then obtain a risk value (e.g., on a scale of 1 to 3) based on the probabilistic value. Further, the plurality of features (e.g., feature values of Andrea Adams between January-December 2019) can be inputted into the model(s) 246 to obtain probabilistic values associated with a plurality of reasons for the medical event (e.g., a prediction of why Andrea Adams will have an ED visit between January-June 2020). The system can then identify the primary reason(s) for the ED visit based on the probabilistic values.

Further, the plurality of features (e.g., feature values of Andrea Adams between January-December 2019) can be inputted into the model(s) 242 to obtain a probabilistic value indicating whether the ED visit is preventable. The system can then obtain an intercepability value based on the probabilistic value. In some embodiments, the system can obtain the intercepability value based on the predicted reason for the ED visit. For example, different clinical factors can be pre-associated with different intercepability values.

In some embodiments, the system can automatically assign the new patient to an outreach effort (e.g., a follow-up, a check-in) if the risk value is above a predefined threshold (i.e., the medical event is likely to occur), if the intercepability value is above a predefined threshold (i.e., the medical event is likely to be preventable), or a combination thereof. In some embodiments, the system automatically assigns the patient to a care provider and provides personalized information (e.g., the predicted reason for the medical event, the time frame) to the care provider. In some embodiments, the system includes an additional machine-learning model trained to recommend outreach efforts to optimize patient outcomes.

In some embodiments, the system automatically refreshes the displayed predictions on the user interface as updated data on the patients is collected. For example, after new healthcare encounters by patients or changes in patient condition, the plurality of features of the patients are re-calculated and re-inputted into the models to obtain updated risk scores, updated reasons for predicted risk, and updated interceptability values. The models themselves can also be updated as new data from new time periods are collected; the new data is used to create a new set of features and outcomes for the patients, which are then used, in conjunction with the original data, to train the models again.

In some embodiments, models such as SVM can provide the risk value, the reason, and interceptability value in formats other than probabilistic values.

In some embodiments, the set of models can predict other auxiliary information. For example, other auxiliary information that could be predicted include how many times the event will occur in the outcome period, when the first event will occur, the cost of the events, if the events will lead to further complications (e.g., if the event is ED visit, predict if the ED visit will lead to hospitalization), etc.

FIG. 5 illustrates process 500 for providing personalized prediction and prevention of medical events (e.g., ED visits) using machine-learning algorithms, in accordance with some embodiments. Process 500 is performed, for example, using one or more electronic devices implementing a software platform. In some examples, process 500 is performed using a client-server system, and the blocks of process 500 are divided up in any manner between the server and a client device. In other examples, the blocks of process 500 are divided up between the server and multiple client devices. Thus, while portions of process 500 are described herein as being performed by particular devices of a client-server system, it will be appreciated that process 500 is not so limited. In other examples, process 500 is performed using only a client device or only multiple client devices. In process 500, some blocks are, optionally, combined, the order of some blocks is, optionally, changed, and some blocks are, optionally, omitted. In some examples, additional steps may be performed in combination with the process 500. Accordingly, the operations as illustrated (and described in greater detail below) are exemplary by nature and, as such, should not be viewed as limiting.

At block 502, a system (e.g., one or more electronic devices) obtains a plurality of feature values of the patient; at block 504, the system provides the plurality of feature values to a set of one or more trained machine-learning models to obtain: a first probabilistic value indicating a likelihood of a future medical event, a second probabilistic value indicating a likelihood of a reason for the future medical event, a third probabilistic value indicating a likelihood that the future medical event can be prevented; at block 506, the system displays, on the display, a risk value of the future medical event based on the first probabilistic value, a reason of the future medical event based on the second probabilistic value, an interceptability value of the future medical event based on the third probabilistic value.

Figure 6:
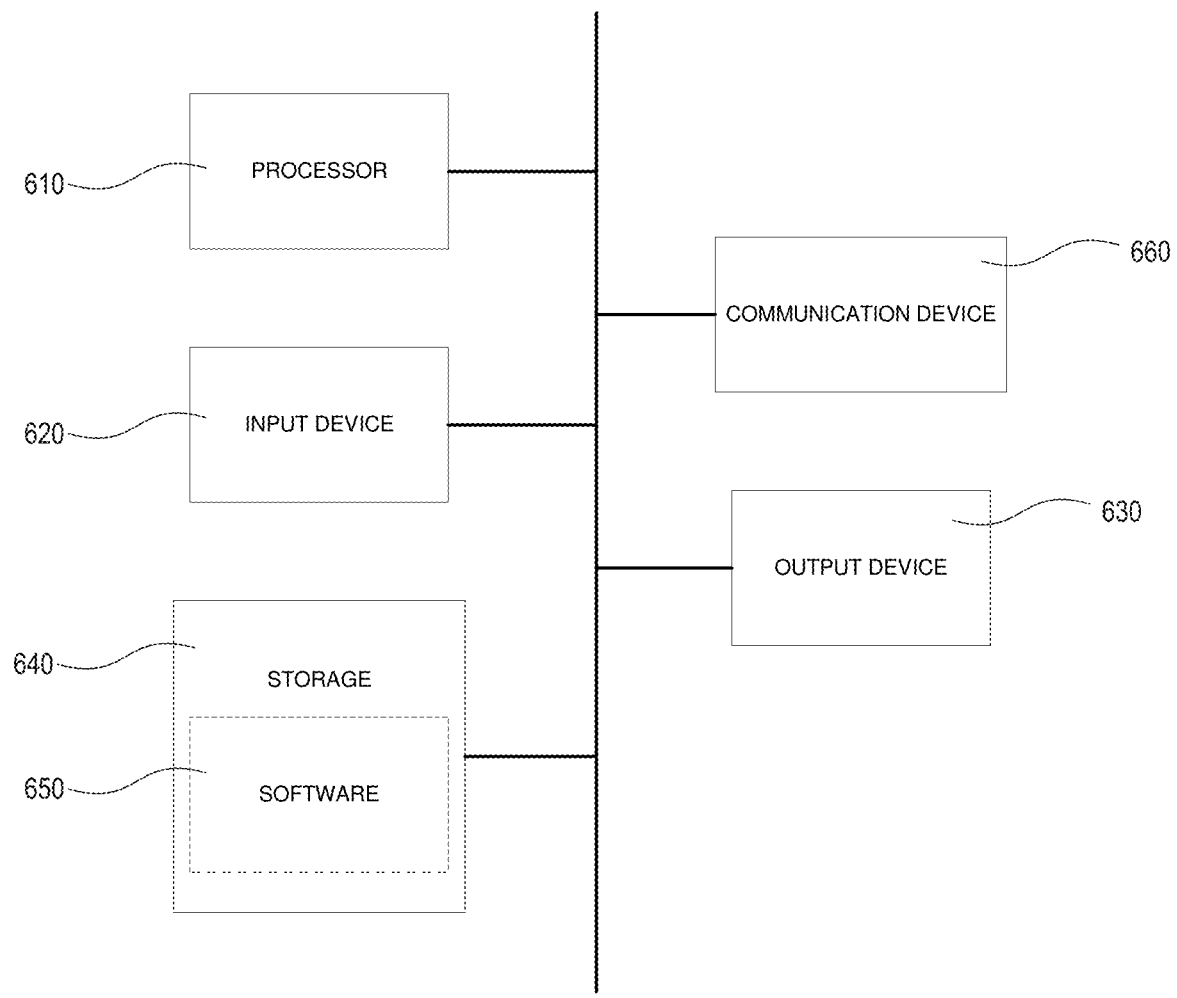
FIG. 6 depicts an exemplary electronic device, in accordance with some embodiments.

The operations described above with reference to FIG. 5 are optionally implemented by components depicted in FIG. 6.

FIG. 6 illustrates an example of a computing device in accordance with one embodiment. Device 600 can be a host computer connected to a network. Device 600 can be a client computer or a server. As shown in FIG. 6, device 600 can be any suitable type of microprocessor-based device, such as a personal computer, workstation, server or handheld computing device (portable electronic device) such as a phone or tablet. The device can include, for example, one or more of processor 610, input device 620, output device 630, storage 640, and communication device 660. Input device 620 and output device 630 can generally correspond to those described above, and can either be connectable or integrated with the computer.

Input device 620 can be any suitable device that provides input, such as a touch screen, keyboard or keypad, mouse, or voice-recognition device. Output device 630 can be any suitable device that provides output, such as a touch screen, haptics device, or speaker.

Storage 640 can be any suitable device that provides storage, such as an electrical, magnetic or optical memory including a RAM, cache, hard drive, or removable storage disk. Communication device 660 can include any suitable device capable of transmitting and receiving signals over a network, such as a network interface chip or device. The components of the computer can be connected in any suitable manner, such as via a physical bus or wirelessly.

Software 650, which can be stored in storage 640 and executed by processor 610, can include, for example, the programming that embodies the functionality of the present disclosure (e.g., as embodied in the devices as described above).

Software 650 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 640, that can contain or store programming for use by or in connection with an instruction execution system, apparatus, or device.

Software 650 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 600 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 600 can implement any operating system suitable for operating on the network. Software 650 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

What is claimed is:

1. A computer-implemented method for providing personalized predictions of medical events for a patient, comprising: at an electronic device with a display,
    obtaining a plurality of feature values of the patient;
    providing the plurality of feature values to a first trained machine-learning model, a second trained machine-learning model, and a third trained machine-learning model;
    determining, using one or more layers associated with the first trained machine-learning model, a first probabilistic value indicating a likelihood of a future medical event;
    determining, using one or more layers associated with the second trained machine-learning model, a second probabilistic value indicating a likelihood of a reason for the future medical event;
    determining, using one or more layers associated with the third trained machine-learning model, a third probabilistic value indicating a likelihood that the future medical event can be prevented,
    wherein a portion of the first trained machine-learning model, a portion of the second trained machine-learning model, and a portion of the third trained machine-learning model have a shared structure and are trained via multi-task learning, and
    wherein the first machine-learning model, the second machine-learning model, and the third machine-learning model are trained by:
        training the shared structure of the first machine-learning model, the second machine-learning model, and the third machine-learning model, and
        training a task-specific portion of the first machine-learning model, a task-specific portion of the second machine-learning model, and a task-specific portion of the third machine-learning model separately;
    displaying, on the display,
        a risk value of the future medical event based on the first probabilistic value,
        a reason of the future medical event based on the second probabilistic value,
        an interceptability value of the future medical event based on the third probabilistic value.

2. The method of claim 1, wherein the first machine-learning model, the second machine-learning model, or the third machine-learning model is trained with a set of training data comprising:
    for each patient of a plurality of patients:
        a feature set corresponding to the respective patient and a first time period, and
        an outcome set corresponding to the respective patient and a second time period.

3. The method of claim 1, wherein the plurality of feature values comprises enrolment and demographic information of the patient, medical information of the patient, information of the patient's care providers, social determinants of health, epidemiological data, billing or claims history information or any combination thereof.

4. The method of claim 1, wherein at least one of the first machine-learning model, the second machine-learning model, and the third machine-learning model comprises a neural network.

5. The method of claim 1, wherein the medical event is a visit to an emergency department, a hospital admission, progression of chronic disease, complication of chronic disease, exacerbation of health conditions and state, or transition from low cost to high cost.

6. The method of claim 1, wherein the displaying is responsive to a user selection of the medical event from a plurality of medical events.

7. The method of claim 1, wherein the first machine-learning model, the second machine-learning model, and the third machine-learning model are used in an ensemble learning architecture.

8. The method of claim 1, further comprising:
    automatically assigning the patient to an outreach effort based on the risk value of the future medical event or the reason of the future medical event.

9. The method of claim 1, wherein the first probabilistic value is indicative of a likelihood of the future medical event occurring within a predefined time period.

10. The method of claim 1, wherein the first machine-learning model, the second machine-learning model, and the third machine-learning model comprise:
    a first single model for predicting a risk, a reason, and interceptability for a first medical event; and
    a second single model for predicting a risk, a reason, and interceptability for a second medical event.

11. The method of claim 1, wherein the first machine-learning model, the second machine-learning model, and the third machine-learning model comprise:
    a first single model for predicting risks for a first medical event and a second medical event;
    a second single model for predicting reasons for the first medical event and the second medical event; and
    a third single model for predicting interceptabilities for the first medical event and the second medical event.

12. The method of claim 1, wherein the interceptability value is based on the reason of the future medical event.

13. The method of claim 1, wherein the first machine-learning model, the second machine-learning model, and the third machine-learning model are trained by optimization for a multivariate error metric.

14. An electronic device, comprising:
    a display;
    one or more processors;
    a memory; and
    one or more programs, wherein the one or more programs are stored in the memory and configured to be executed by the one or more processors, the one or more programs including instructions for:
        obtaining a plurality of feature values of the patient;
        providing the plurality of feature values to a first trained machine-learning model a second trained machine-learning model, and a third trained machine-learning model;
        determining, using one or more layers associated with the first trained machine-learning model, a first probabilistic value indicating a likelihood of a future medical event;
        a determining, using one or more layers associated with the second trained machine-learning model, a second probabilistic value indicating a likelihood of a reason for the future medical event;

determining, using one or more layers associated with the third trained machine-learning model, a third probabilistic value indicating a likelihood that the future medical event can be prevented, wherein a portion of the first trained machine-learning model, a portion of the second trained machine-learning model, and a portion of the third trained machine-learning model have a shared structure and are trained via multi-task learning, and wherein the first machine-learning model, the second machine-learning model, and the third machine-learning model are trained by:

training the shared structure of the first machine-learning model, the second machine-learning model, and the third machine-learning model, and training a task-specific portion of the first machine-learning model, a task-specific portion of the second machine-learning model, and a task-specific portion of the third machine-learning model separately;

displaying, on the display, a risk value of the future medical event based on the first probabilistic value, a reason of the future medical event based on the second probabilistic value, an interceptability value of the future medical event based on the third probabilistic value.

15. A non-transitory computer-readable storage medium storing one or more programs, the one or more programs comprising instructions, which when executed by one or more processors of an electronic device having a display, cause the electronic device to:

obtain a plurality of feature values of the patient;

provide the plurality of feature values to a first trained machine-learning model, a second trained machine-learning model, and a third trained machine-learning model;

determine, using one or more layers associated with the first trained machine-learning model, a first probabilistic value indicating a likelihood of a future medical event;

determine, using one or more layers associated with the second trained machine-learning model, a second probabilistic value indicating a likelihood of a reason for the future medical event;

determine, using one or more layers associated with the third trained machine-learning model, a third probabilistic value indicating a likelihood that the future medical event can be prevented, wherein a portion of the first trained machine-learning model, a portion of the second trained machine-learning model, and a portion of the third trained machine-learning model have a shared structure and are trained via multi-task learning, and wherein the first machine-learning model, the second machine-learning model, and the third machine-learning model are trained by:

training the shared structure of the first machine-learning model, the second machine-learning model, and the third machine-learning model, and training a task-specific portion of the first machine-learning model, a task-specific portion of the second machine-learning model, and a task-specific portion of the third machine-learning model separately;

display, on the display, a risk value of the future medical event based on the first probabilistic value, a reason of the future medical event based on the second probabilistic value, an interceptability value of the future medical event based on the third probabilistic value.

* * * * *